(12) United States Patent
Omori

(10) Patent No.: US 8,246,633 B2
(45) Date of Patent: Aug. 21, 2012

(54) MEDICAL MANIPULATOR AND MEDICAL ROBOT SYSTEM

(75) Inventor: Shigeru Omori, Ashigarakami-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 1007 days.

(21) Appl. No.: 12/176,000

(22) Filed: Jul. 18, 2008

(65) Prior Publication Data

US 2009/0198253 A1 Aug. 6, 2009

(30) Foreign Application Priority Data

Feb. 1, 2008 (JP) ................................. 2008-022669

(51) Int. Cl.
*A61B 19/00* (2006.01)
(52) U.S. Cl. .................. 606/130; 318/568.11; 483/901; 901/15
(58) Field of Classification Search ............. 318/568.11; 483/901; 600/429; 606/33, 130; 901/15
See application file for complete search history.

(56) References Cited

U.S. PATENT DOCUMENTS

| | | | |
|---|---|---|---|
| 4,494,539 A | | 1/1985 | Zenitani et al. |
| 5,351,676 A | * | 10/1994 | Putman ......................... 600/117 |
| 5,876,325 A | * | 3/1999 | Mizuno et al. ................. 600/102 |
| 6,331,181 B1 | | 12/2001 | Tierney et al. |
| 6,840,938 B1 | * | 1/2005 | Morley et al. .................. 606/51 |
| 6,889,116 B2 | | 5/2005 | Jinno |
| 2005/0216033 A1 | * | 9/2005 | Lee et al. ....................... 606/130 |
| 2005/0222554 A1 | * | 10/2005 | Wallace et al. ................. 606/1 |
| 2009/0157092 A1 | * | 6/2009 | Blumenkranz et al. ........ 606/130 |

FOREIGN PATENT DOCUMENTS

| | | |
|---|---|---|
| JP | 1-20617 | 4/1989 |
| JP | 1-20619 | 4/1989 |
| JP | 2002-102248 | 4/2002 |
| JP | 2003-61969 | 3/2003 |

OTHER PUBLICATIONS

Shinya Okabe, et al, "Improvement on the Input Impedance of a Coaxial-Slot Antenna for Interstitial Heating by Loading a Matching Circuit", IECEI transactions, vol. J87-B, No. 10, Oct. 2004, pp. 1741-1748, with partial English Translation.

* cited by examiner

*Primary Examiner* — Nicholas Lucchesi
*Assistant Examiner* — Gerald Landry, II
(74) *Attorney, Agent, or Firm* — Oblon, Spivak, McClelland, Maier & Neustadt, L.L.P.

(57) ABSTRACT

A manipulator includes a yaw axis and a pitch axis disposed as joints on a distal end of a joint shaft and which are actuatable by motors, a needle variable in orientation by the joints, a coaxial connector disposed at a position closer to a proximal end of the manipulator than the joint shaft, and a coaxial cable providing within the joint shaft at least a portion of an electrical connection between the coaxial connector and the needle. A small board providing an impedance matching circuit, and which includes a coil and a capacitor, is interposed between the coaxial connector and the coaxial cable.

13 Claims, 19 Drawing Sheets

MEDICAL MANIPULATOR AND MEDICAL ROBOT SYSTEM

BACKGROUND OF THE INVENTION

1. Field of the Invention

The present invention relates to a medical manipulator that includes a needle mounted on the tip end of a shaft for supplying microwave energy to perform a surgical technique on an affected region of a patient, and also to a medical robot system incorporating such a medical manipulator.

2. Description of the Related Art

Electrosurgical knives and laser knives mainly are used to solidify, stop bleeding, and cut off affected and surrounding regions in patients. Recently, there has been proposed a medical apparatus employing microwaves. The proposed medical apparatus includes a needle for piercing a living body and a means for supplying microwave energy to the needle so as to enable the needle to generate thermal energy to perform a surgical technique, such as tissue solidification, blood stanching, or the like, on the living tissue (see, for example, Japanese Patent Publication No. 1-020617 and Japanese Patent Publication No. 1-020619).

A medical apparatus of the type described above is capable of easily stopping bleeding and thermally modifying living tissue without causing the living tissue to be carbonized. Heat that is generated in the tissue by microwaves kills bacteria and prevents wasteful bleeding.

According to a recent endoscopic surgical operation process, small holes are opened in the abdominal region, for example, of a patient, and an endoscope and manipulators or forceps are inserted into such holes. The surgeon performs a surgical operation on the patient with the manipulators or forceps, while watching an image captured by the endoscope and displayed on a display monitor. Since the endoscopic surgical operation process does not require a laparotomy to be performed, the operation is less burdensome on the patient and greatly reduces the number of days required for the patient to spend in the hospital before recovering from the operation and being released from the hospital. Therefore, the range of surgical operations in which the endoscopic surgical operation process may be applied is expected to increase.

As disclosed in Japanese Laid-Open Patent Publication No. 2002-102248 and Japanese Laid-Open Patent Publication No. 2003-061969, a manipulator system comprises a manipulator and a controller for controlling the manipulator. The manipulator comprises an operating unit, which is manually operated, and a working unit replaceably mounted on the operating unit.

There has also been proposed a medical robot system for actuating a medical manipulator with a robot arm (see, for example, U.S. Pat. No. 6,331,181). The medical robot system can be remotely controlled by a master arm, and can be moved in various ways under a programmed control.

The medical robot arm has a plurality of robot arms, which can selectively be used depending on the surgical technique required. One of the robot arms incorporates an endoscope therein for capturing an image representing the inside of a body cavity, which is capable of being visually confirmed on a display monitor.

The literature, "Improvement on the input impedance of a coaxial-slot antenna for interstitial heating by loading a matching circuit", by Shinya Okabe and three others, IECEI transactions 2004/10, Vol. J87-B, No. 10, pp. 1741-1748, shows a medical coaxial slot antenna for interstitial heating, which is combined with a matching circuit for matching the input impedance. The coaxial slot antenna has two slots capable of producing a locally heated region, another slot (matching slot) for impedance matching, and a metal pipe covering the matching slot.

The medical apparatus disclosed in Japanese Patent Publication No. 1-020617 and Japanese Patent Publication No. 1-020619 basically is premised on a laparotomy operation, and does not take into account endoscopic surgical operations using forceps. There has heretofore been proposed an electrosurgical knife, which is mounted on the tip end of forceps and connected to electric wires. However, even if the electrosurgical knife is replaced with a needle for supplying microwaves, since microwave energy tends to radiate from the electrical wires, the assembly is considerably inefficient.

If microwaves are supplied to a plurality of needles, which are appropriately spaced apart from each other, then it may be contemplated that the needles can perform a surgical technique over a wide region, thereby resulting in a synergetic effect and a shortened operation time. However, in endoscopic surgical operations, since forceps are inserted through narrow trocars, even if needles are mounted onto the tip ends of such forceps, the distance between the needles is limited.

SUMMARY OF THE INVENTION

It is an object of the present invention to provide a medical manipulator, which is capable of efficiently supplying energy to a needle mounted on the tip end thereof, as well as to provide a medical robot system incorporating such a medical manipulator.

Another object of the present invention is to provide a medical manipulator, which can easily be inserted through a trocar for use in endoscopic surgical operations, and which allows a plurality of needles to pierce a living body at appropriately spaced locations.

A medical manipulator according to an aspect of the present invention includes a shaft, at least one joint mounted on a distal end of the shaft and which is actuatable by an actuator, a needle variable in orientation by the joint, a connector disposed at a position closer to a proximal end of the manipulator than the shaft, and a coaxial cable providing at least a portion of an electrical connection between the connector and the needle.

Since at least a portion of the electrical connection between the connector and the needle is provided by the coaxial cable, the microwave energy supplied to the needle is prevented from being unduly radiated. The connector also allows the medical manipulator to be detachably connected to a microwave oscillation source.

The coaxial cable may be disposed at least within the shaft or on a portion along the shaft. The shaft of the medical manipulator must have a certain length, since it is inserted through a trocar into a body cavity. The coaxial cable in the shaft is effective to prevent microwave energy from being radiated.

The coaxial cable may include two poles, one of the two poles comprising an external tubular covering conductor, wherein at least a portion of the external tubular covering conductor comprises a metal tube. Since the coaxial cable is not bent within the shaft, for example, the coaxial cable is not required to be flexible within the shaft. If an external conductor of the coaxial cable comprises a metal tube, then the coaxial cable is less costly to manufacture and simpler in structure. The metal tube does not require a water resistance means, since body fluids of the patient and cleaning solutions tend not to penetrate into the metal tube.

If the medical manipulator includes a circuit comprising an inductive means and a capacitive means interposed between the connector and the coaxial cable, then the circuit can be used to adjust impedance. The term "circuit" is used herein in a wide sense, and is not limited to a circuit on a board.

The medical manipulator may further comprise a microwave oscillation source connected to the connector, wherein the circuit comprises a matching circuit for substantially equalizing the output impedance of the microwave oscillation source and the input impedance of the coaxial connector while the needle pierces a living body. With the impedances being thus matched, microwave reflections are reduced, and microwave energy can be supplied efficiently to the needle.

The medical manipulator may further comprise a circuit interposed between the connector and the coaxial cable, wherein the circuit includes a metal pipe.

The needle may be used to cauterize living tissue of a living body when the needle is supplied with microwave energy while piercing the living body. When living tissue is cauterized, the living tissue is thermally modified without being carbonized, and bleeding from the living tissue is stopped with ease.

The medical manipulator may further comprise a plurality of microwave supply means, each of which comprises a needle, a coaxial cable, and a connector. The needles may be pushed in to pierce the living tissue simultaneously at different locations, so that the living tissue can be cauterized more efficiently.

According to another aspect of the present invention, a medical manipulator comprises a shaft, a plurality of needles mounted on a distal end of the shaft, and a needle spacing means for spacing the needles apart from each other. The needle spacing means allows the needles to pierce the living tissue simultaneously at spaced locations, resulting in a synergetic effect. Before the needles are spaced apart by the needle spacing means, the needles can be positioned closely to each other and hence can easily be inserted into a trocar.

The needle spacing means may comprise resilient members for normally urging the needles apart from each other. The resilient members are simple in structure while allowing the needles to be moved automatically when the needles pass through the trocar.

The needle spacing means may further comprise link mechanisms for displacing the needles while holding the needles in substantially the same orientation. The link mechanisms keep the needles in substantially the same orientation, and thus make it easy for the needles to pierce the living body.

The needle spacing means may also comprise arms, which are tiltable to return the needles closely toward each other in abutment against an end of the trocar when the shaft is pulled out from the trocar. The arms allow the shaft and the needles to be easily pulled out from the trocar.

According to still another aspect of the present invention, there is also provided a medical robot system comprising a medical manipulator including a shaft and at least one joint mounted on a distal end of the shaft and which is actuatable by an actuator, a robot arm holding the medical manipulator, and a controller for controlling the medical manipulator and the robot arm, wherein the medical manipulator comprises a needle variable in orientation by the joint, a connector disposed at a position closer to a proximal end of the manipulator than the shaft, and a coaxial cable providing at least a portion of an electrical connection between the connector and the needle.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
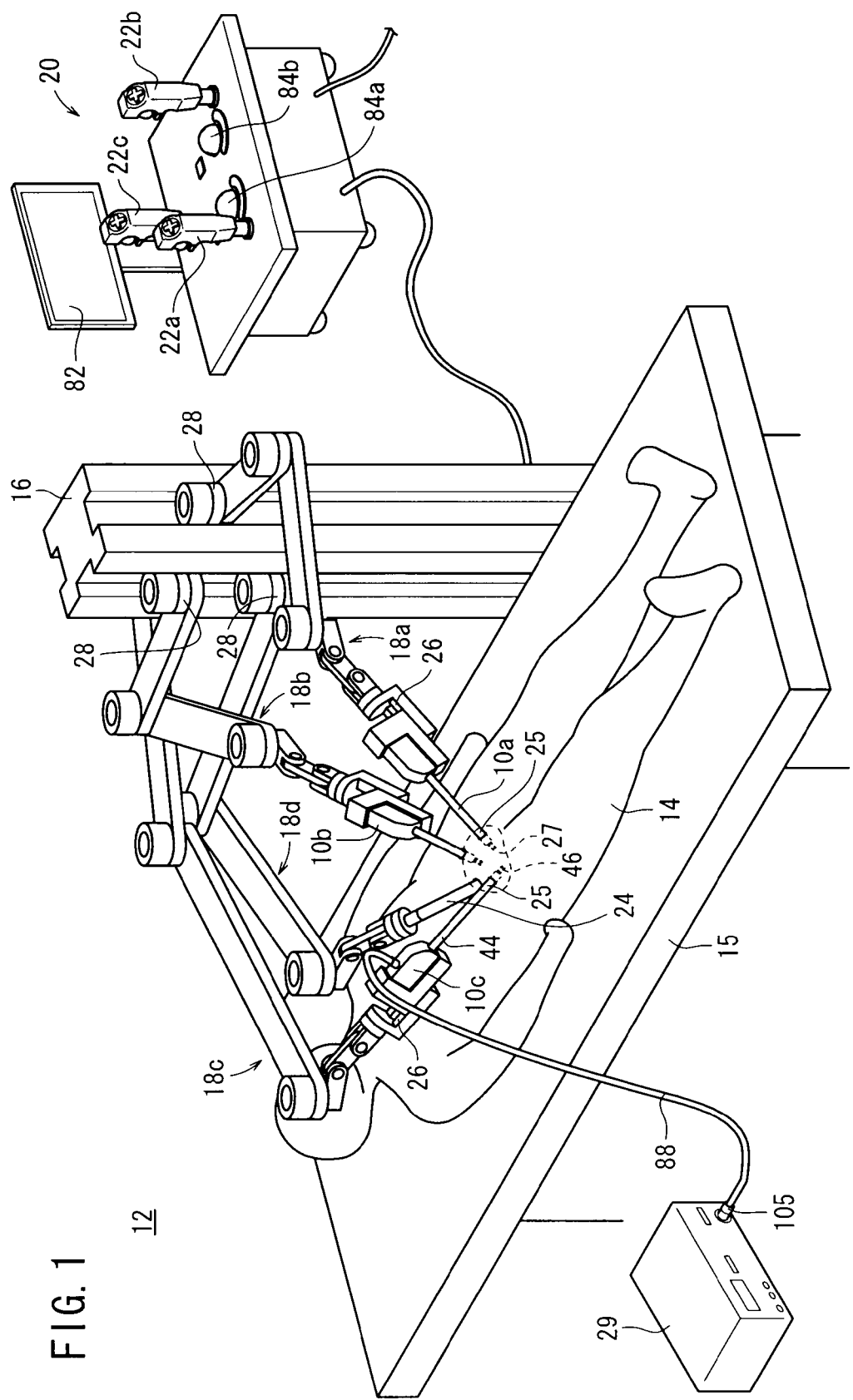
FIG. 1 is a perspective view of a medical robot system according to an embodiment of the present invention.

Like or corresponding parts shall be denoted by like or corresponding reference characters throughout the views.

Medical manipulators and medical robot systems according to embodiments of the present invention will be described below with reference to FIGS. 1 through 19.

As shown in FIG. 1, a medical manipulator 10c and a medical robot system 12 according to an embodiment of the present invention are particularly suitable for performing an endoscopic surgical operation on a patient (also referred to as a "living body") 14.

The medical robot system 12 comprises a station 16 in the form of a vertical column disposed near a surgical bed 15, four robot arms 18a, 18b, 18c, 18d mounted on the station 16, and a console (controller) 20 for controlling the medical robot system 12 in its entirety. The robot arms 18a through 18d and the console 20 may be connected to each other through a communication means comprising a wired link, a wireless link, a network, or a combination thereof. The console 20 is not required to control the medical robot system 12 in its entirety, but rather, the robot arms 18a through 18d may be feedback-controlled by internal controllers combined with the medical robot system 12. The robot arms 18a through 18d may be actuated under the control of the console 20 for being operated according to automatic programmed operations, or may be manually actuated by respective joysticks 20a, 20b, 20c provided on the console 20. The robot arms 18a through 18d also may be actuated through a combination of automatic programmed operations and manually controlled operations.

The robot arms 18a through 18c have manipulators 10a, 10b, 10c disposed respectively on distal ends thereof. The robot arm 18d has an endoscope 24 on the distal end thereof. The manipulators 10a through 10c and the endoscope 24 are inserted into a body cavity 27 of the patient 14 through respective trocars 25. The station 16 may comprise a plurality of stations supporting the respective robot arms 18a through 18d. The manipulators 10a through 10c and the endoscope 24 are removably mounted onto the respective robot arms 18a through 18d.

Each of the robot arms 18a through 18d makes up an articulated mechanism, e.g., a mechanism with six independent axes. The robot arms 18a through 18d are controlled by the console 20, so as to set the manipulators 10a through 10c and the endoscope 24 at arbitrary postures and at arbitrary positions, within the operating ranges of the robot arms 18a through 18d. The robot arms 18a through 18d include respective slide mechanisms 26 for moving the manipulators 10a through 10c and the endoscope 24 back and forth along at least the axes defined by the distal ends thereof, and respective lifting and lowering mechanisms 28, which are movable vertically along the station 16. The robot arms 18a through 18d may be structurally identical to each other, or may have different structures depending on the types of manipulators 10a through 10c and the endoscope 24 that are utilized.

The manipulators 10a, 10b, which are mounted respectively on the robot arms 18a, 18b, serve to perform direct surgical techniques on an affected region of the patient 14. A gripper and scissors, for example, are mounted respectively onto distal-end working units of the manipulators 10a, 10b. The manipulator 10c mounted on the robot arm 18c serves to perform a surgical technique for applying microwaves supplied from a microwave generator 29 to an affected region, e.g., the liver, of the patient 14. Alternatively, a manipulator such as a retractor may be mounted on the robot arm 18c for retracting an organ within a body cavity 27 or the like to a given place to allow the surgeon to have a wider operative field. The microwave generator 29 may be integrally combined with the console 20.

Figure 2:
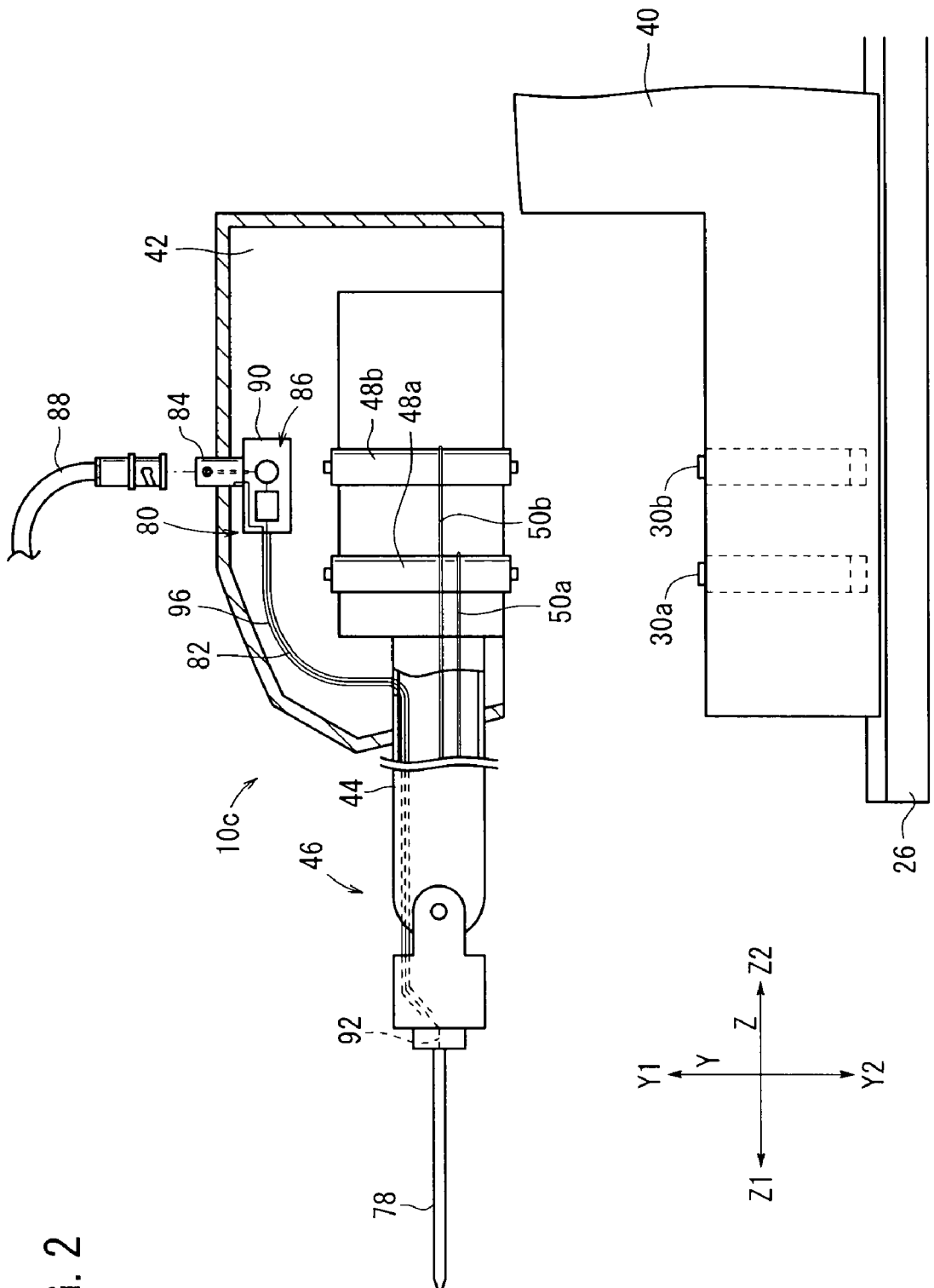
FIG. 2 is a side elevational view, partly in cross section, of a medical manipulator according to an embodiment of the present invention.
Figure 4:
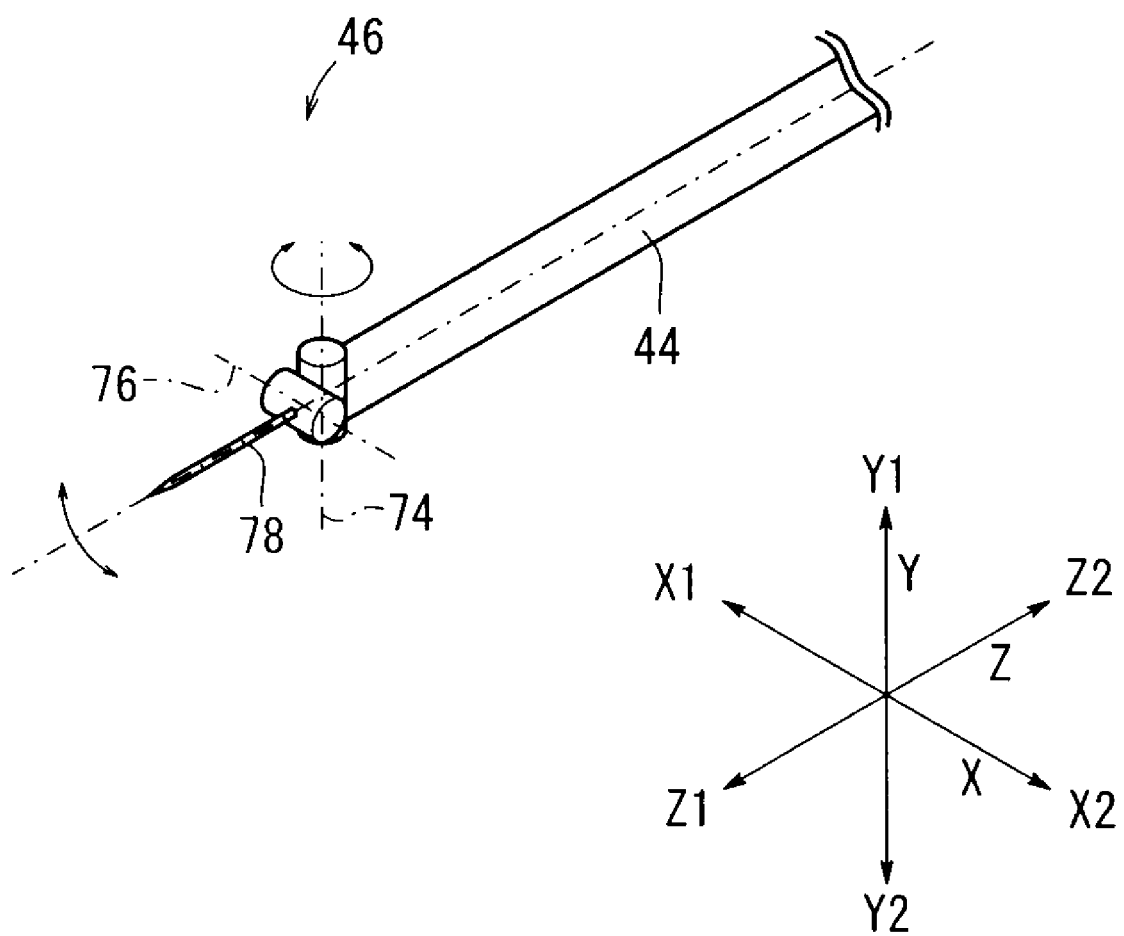
FIG. 4 is a perspective view of the distal-end working unit.

Further structural details of the manipulator 10c shall be described below. As shown in FIGS. 2 and 4, it is assumed that directions established with respect to the manipulator 10c include X directions representing horizontal transverse directions of the manipulator 10c, Y directions representing vertical transverse directions of the manipulator 10c, and Z directions representing longitudinal directions of the manipulator 10c, i.e., the connector shaft (rod-shaped member) 44 thereof. The X directions include an X1 direction representing a rightward direction as viewed from the front of the manipulator 10c and an X2 direction representing a leftward direction as viewed from the front of the manipulator 10c. The Y directions include a Y1 direction representing an upward direction and a Y2 direction representing a downward direction. The Z directions include a Z1 direction representing a forward direction and a Z2 direction representing a rearward direction.

As shown in FIG. 2, the manipulator 10c is removably mounted on a slider 40, which is disposed on the distal end of the robot arm 18c. The slider 40 is slidable in the Z directions at the distal end of the robot arm 18c. The slider 40 supports two motors (actuators) 30a, 30b mounted therein in an array along the Z directions.

The manipulator 10c comprises a connecting block 42 for connection to the slider 40, a hollow joint shaft 44 extending from the connecting block 42 in the Z1 direction, and a distal-end working unit 46 mounted on the distal end of the joint shaft 44.

The connecting block 42 is removably and replaceably mounted on the slider 40 by a removable mounting mechanism. The connecting block 42 supports pulleys 48a, 48b mounted thereon in an array along the Z directions and held in engagement with the respective motors 30a, 30b. The motors 30a, 30b or the pulleys 48a, 48b have noncircular teeth, while the pulleys 48a, 48b or the motors 30a, 30b have noncircular recesses. The noncircular teeth engage with the respective noncircular recesses for transmitting rotation of the motors 30a, 30b to the pulleys 48a, 48b.

Wires 50a, 50b are trained respectively around the pulleys 48a, 48b. The wires 50a, 50b are annular in shape, wherein portions thereof are fixed to the pulleys 48a, 48b for preventing slippage on the pulleys 48a, 48b. The wires 50a, 50b are trained in 1.5 turns around the pulleys 48a, 48b, and extend in the Z1 direction inside the joint shaft 44. When the pulleys 48a, 48b are rotated about their own axes by the motors 30a, 30b, one of the wires 50a, 50b is wound around the corresponding pulley, while the other wire is paid out from the other corresponding pulley. The wires 50a, 50b are spaced from each other in the Z directions, so as to be held out of interference with each other.

Figure 3:
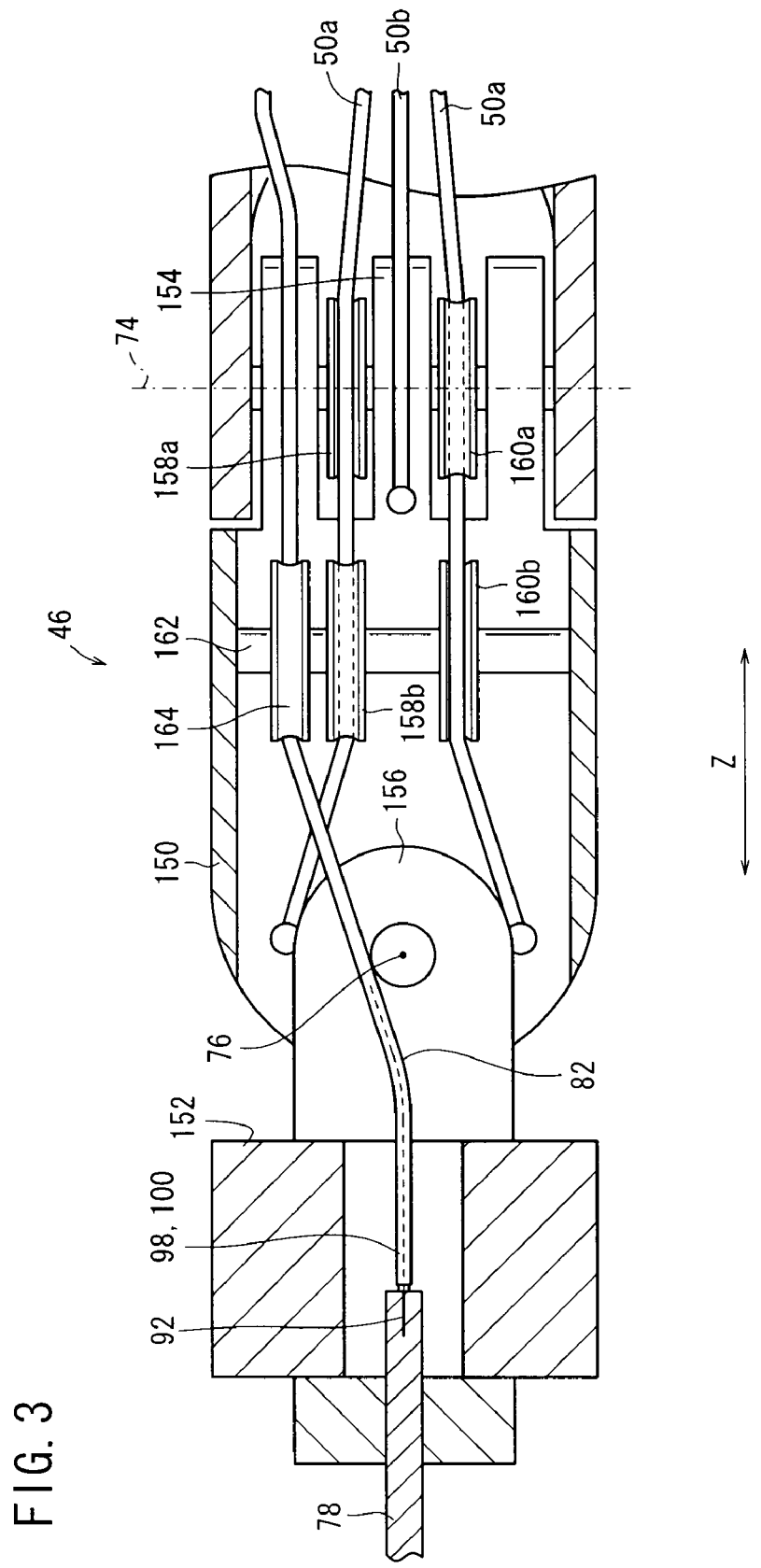
FIG. 3 is a longitudinal cross-sectional view of a distal-end working unit of the medical manipulator.

As shown in FIG. 3, the distal-end working unit 46 comprises a pitch-direction swinging member 150 and a yaw-direction swinging member 152. The pitch-direction swinging member 150 has a proximal end thereof swingably supported on the joint shaft 44 by means of a semicircular member 154 that projects rearwardly from the pitch-direction swinging member 150, and rotatably supported on a yaw shaft (also referred to as yaw axis) 74. The semicircular member 154 has upper and lower ends, to which ends of the wire 50b are fixedly connected. When the wire 50b is displaced back and forth, the pitch-direction swinging member 150 is angularly moved about the yaw shaft 74.

The yaw-direction swinging member 152 has a proximal end, which is swingably supported on the pitch-direction swinging member 150 by means of a semicircular member 156 that projects rearwardly from the yaw-direction swinging member 152, and is rotatably supported on a pitch shaft (also referred to as a pitch axis) 76. The semicircular member 156 includes left and right ends, to which the ends of the wire 50a are fixedly connected. When the wire 50a is displaced back and forth, the yaw-direction swinging member 152 is angularly moved about the pitch axis 76.

One of the end portions of the wire 50a is trained in an S shape around two pulleys 158a, 158b that are arrayed in the Z directions. The other end portion of the wire 50a is trained in an S shape around two pulleys 160a, 160b that are arrayed in the Z directions. The pulleys 158a, 160a are rotatably supported on the yaw shaft 74, while the pulleys 158b, 160b are rotatably supported on a shaft 162, which is disposed in the pitch-direction swinging member 150 parallel to the yaw shaft 74.

A coaxial cable 82 is trained in an approximate half turn around a pulley 164 that is rotatably supported on the shaft 162, and extends toward a needle 78. As shown in FIG. 3, the coaxial cable 82 includes a mesh shield 98 and an external covering sheath 100, which cover a conductive core wire 92 up to a position near the needle 78.

As shown in FIG. 4, the distal-end working unit 46 is mounted on a distal end of the joint shaft 44 for actuating the pitch-direction swinging member 150 about the yaw axis 74, and for actuating the yaw-direction swinging member 152 about the pitch axis 76.

The conductive core wire 92 is insulated from the exterior except for a region thereof where the conductive core wire 92 is connected to the proximal end of the needle 78. When the wires 50a, 50b are moved back and forth upon rotation of the pulleys 48a, 48b, the pulleys in the distal-end working unit 46 are driven and rotated, thereby causing the needle 78 to move about two axes so as to be variable in orientation. The needle 78 undergoes flexural motion about the yaw axis (joint) 74 and the pitch axis (joint) 76, for example. The distal-end working unit 46 may be of the same mechanism as the distal-end working unit of the medical manipulator disclosed in Japanese Laid-Open Patent Publication No. 2003-61969, for example. The distal-end working unit 46 may have at least one axis joint for changing the orientation of the needle 78.

Since the yaw axis 74 and the pitch axis 76 might possibly interfere mutually with one another, the console 20 calculates an amount of interference, and then controls the wires 50a, 50b to move back and forth while compensating for any interfering movements. In other words, the console 20 controls the wires 50a, 50b such that when one of the pitch-direction swinging member 150 and the yaw-direction swinging member 152 is moved, the console 20 prevents the other swinging member from moving into interference with the one that is moved.

As shown in FIG. 2, the joint shaft 44 extends in the Z1 direction from the connecting block 42, and the distal-end working unit 46 is mounted on the distal end of the joint shaft 44. The joint shaft 44 is required to have a certain length, which is sufficiently long to be inserted through the trocar 25 into the body cavity 27.

A microwave supplying means 80 for supplying microwaves from the microwave generator 29 to the needle 78 will be described below.

The microwave supplying means 80 comprises the needle 78, a coaxial connector 84 such as a BNC (Bayonet Neill Concelman) connector, for example, and a small board 90. The small board 90 is of a molded structure, for example, which is resistant to water and rust.

The needle 78 pierces an affected region or a nearby region within the body cavity 27 and applies microwaves to such a region.

The coaxial connector 84 is mounted on an upper wall of the connecting block 42, at a position that is closer to the proximal end of the connector block 42 than the joint shaft 44. The coaxial connector 84 interconnects the microwave supply means 80 and the microwave generator 29 via an external coaxial cable 88. The external coaxial cable 88 has an impedance of 50Ω, for example. The microwave generator 29 generates microwaves having a frequency in a 2.4 GHz band or a 900 MHz band, at an output power level ranging from 30 to 100 W.

The microwave supplying means 80 also includes an impedance matching circuit 86 mounted on the small board 90 in close proximity to the coaxial connector 84 in the connecting block 42. The impedance matching circuit 86 is interposed between the coaxial connector 84 and the coaxial cable 82.

The coaxial cable 82 extends from the connecting block 42 and through the joint shaft 44 across the yaw shaft 74 and the pitch shaft 76. The coaxial cable 82 serves to electrically interconnect the impedance matching circuit 86 and the needle 78. The impedance matching circuit 86 is positioned highly closely to the coaxial connector 84, and the coaxial cable 82 extends substantially the full distance between the coaxial connector 84 and the needle 78. Although the coaxial cable 82 preferably should extend as long as possible between the coaxial connector 84 and the needle 78, due to structural limitations, the coaxial cable 82 may not be able to extend the full distance between the coaxial connector 84 and the needle 78. Therefore, the coaxial cable 82 may extend at least a portion of the full distance between the coaxial connector 84 and the needle 78.

Figure 5:
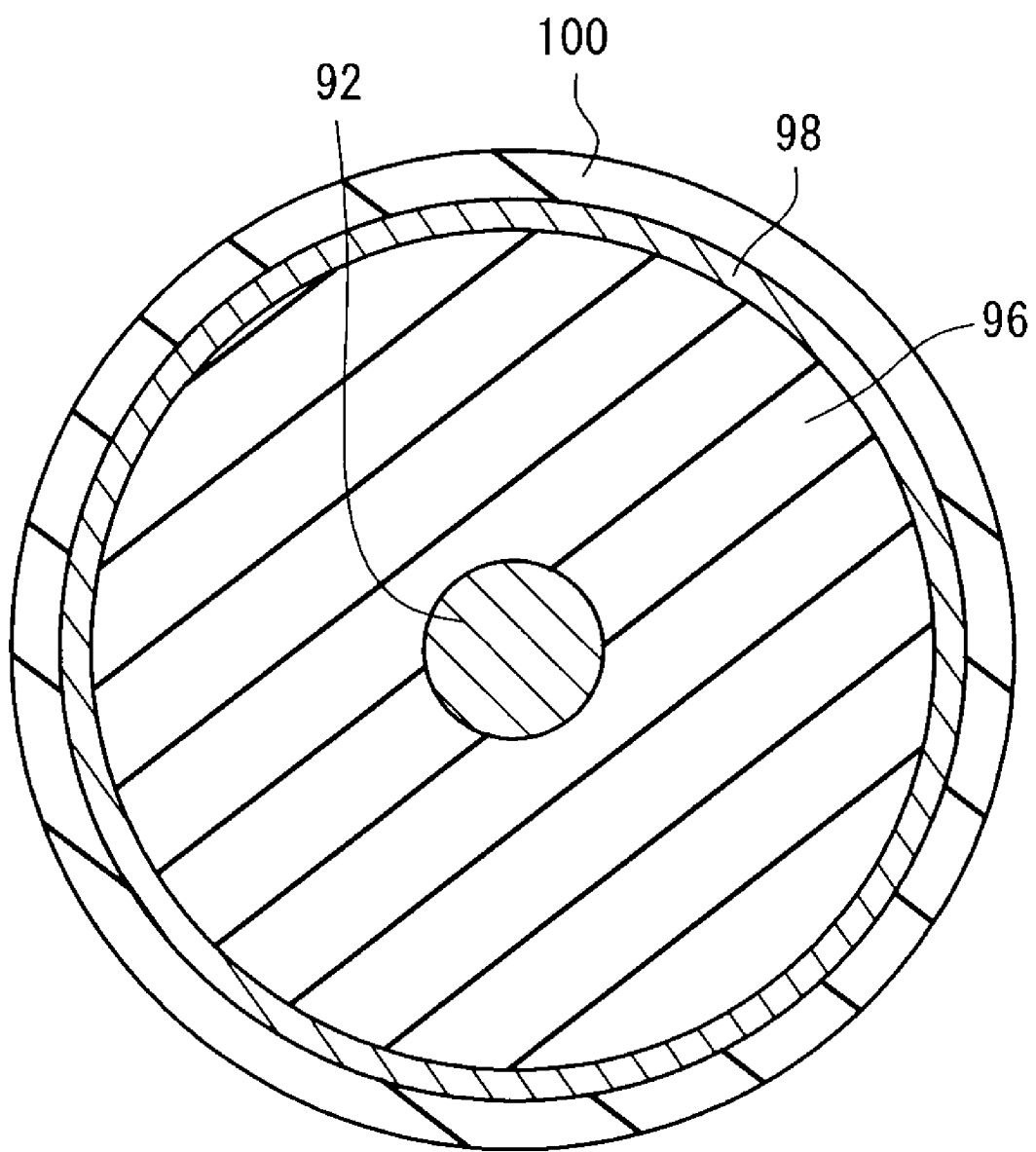
FIG. 5 is a transverse cross-sectional view of a coaxial cable.

As shown in FIG. 5, the coaxial cable 82 is of a coaxial dipole structure around the conductive core wire 92. The coaxial cable 82 includes an insulating layer 96, the mesh shield (outer conductor) 98, and the external covering sheath 100, which are arranged in succession radially outwardly in this order. Since the core wire 92 is shielded by the coaxial mesh shield 98, microwaves supplied to the core wire 92 are prevented from being radiated outwardly.

The core wire 92 is connected to the proximal end of the needle 78. The core wire 92 may be connected to the needle 78 by welding, compression, winding, or any combination thereof.

The coaxial cable 82 has suitable physical strength and flexibility. Thus, the coaxial cable 82 can be placed easily inside the manipulator 10c and can be bent when the pitch-direction swinging member 150 is moved angularly about the yaw axis 74, as well as when the yaw-direction swinging member 152 is moved angularly about the pitch axis 76. The mesh shield 98 comprises a metal mesh and is highly flexible. The coaxial cable 82 is of a sufficiently small diameter to enable placement thereof inside the joint shaft 44, and is smaller in diameter than the external coaxial cable 88. Because of these structural differences, the coaxial cable 82 and the external coaxial cable 88 exhibit different characteristic impedances.

Figure 6:
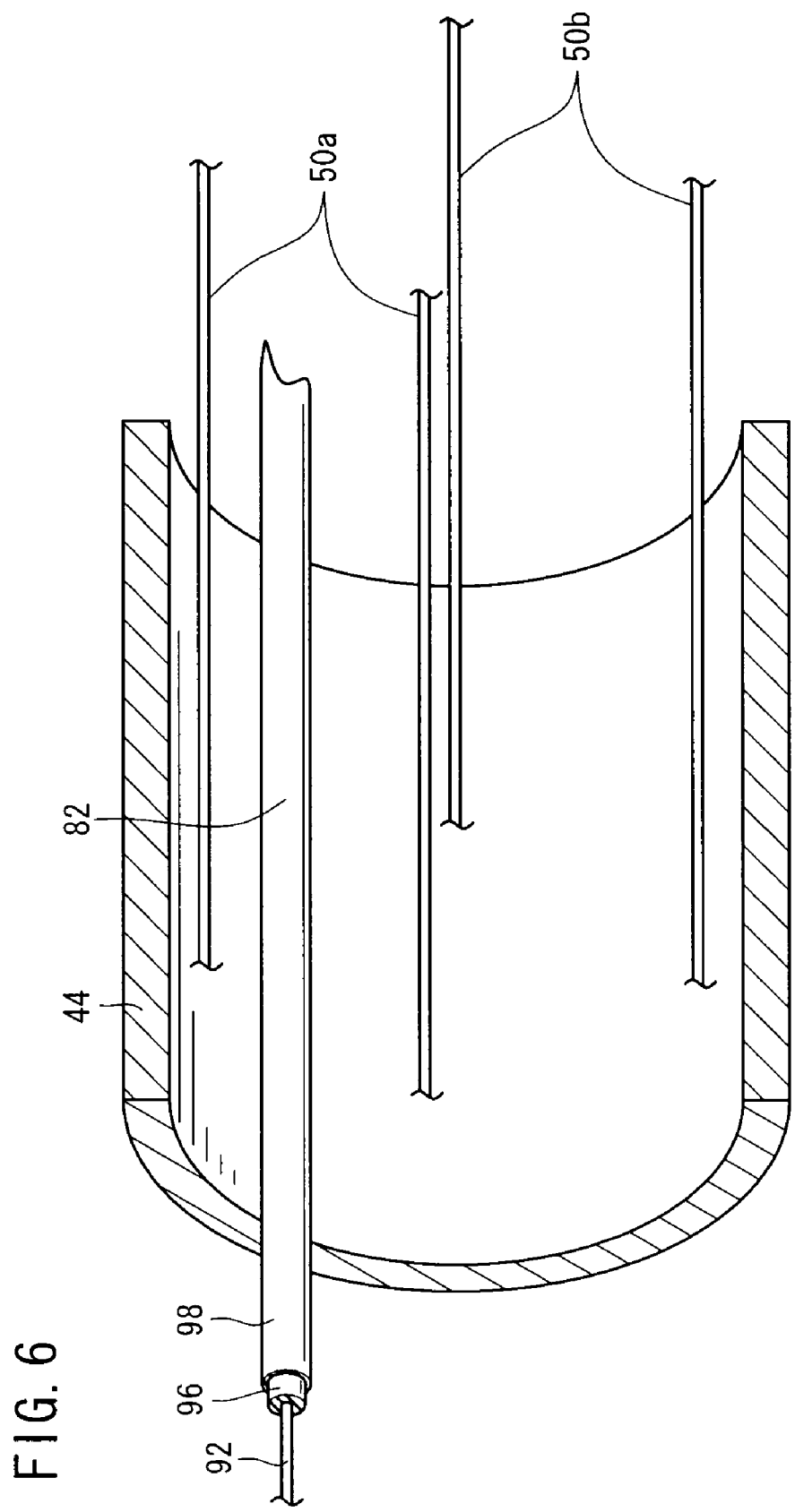
FIG. 6 is a perspective view, partly in cross section, of a connector shaft.

As shown in FIG. 6, at least a portion of the mesh shield 98 may comprise a metal tube. Since the coaxial cable 82 is not bent within the joint shaft 44, the coaxial cable 82 is not required to be flexible inside the joint shaft 44. If at least a portion of the mesh shield 98 comprises a metal tube, then the coaxial cable 82 can be less costly to manufacture as well as simpler in structure. The metal tube does not require any water resistance means, since the body fluid of the patient and cleaning solutions tend not to penetrate into the metal tube. Since the coaxial cable 82 in the joint shaft 44 is not exposed to the exterior, the external covering sheath 100 may be dispensed with. The coaxial cable 82 may be fixed to an inner wall surface of the joint shaft 44 by means of adhesive bonding, welding, fusion, or the like, so that the coaxial cable 82 will not come into contact with the wires 50a, 50b.

Figure 7:
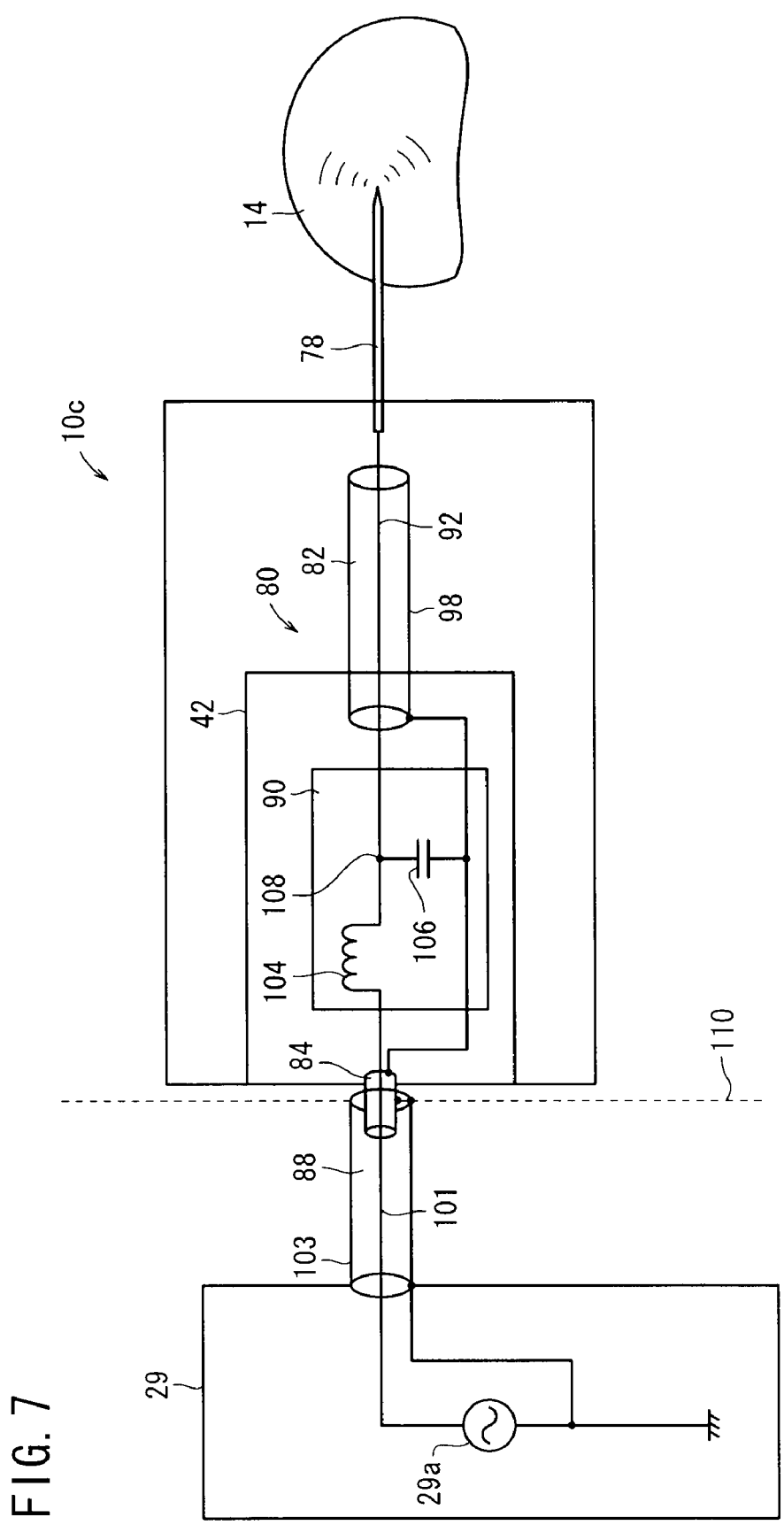
FIG. 7 is a circuit diagram of a microwave supply means of the medical manipulator.

As shown in FIG. 7, the microwave generator 29 includes an oscillator 29a for generating microwaves, the oscillator 29a having one pole (signal line) connected to a core wire 101 of the external coaxial cable 88 and another pole (ground line) set to a ground level and which is connected to a mesh shield 103 of the external coaxial cable 88. The microwave generator 29 and the external coaxial cable 88 are detachably connected to each other through the coaxial connector 105 (see FIG. 1). In FIG. 7, for the sake of brevity, the joint shaft 44, the trocar 25, the body cavity 27, and an ON/OFF switch for supplying microwaves have been omitted from illustration.

The signal line and the ground line are connected to the small board 90 through a central pin and a tubular terminal, respectively, of the coaxial connector 84. The small board 90 comprises a circuit including a coil (inductance means) 104 connected in series to the signal line, and a capacitor (capacitance means) 106 connected between the signal line and the ground line. The coil 104 and the capacitor 106 are connected to each other at a junction 108, which is connected to the core wire 92 of the coaxial cable 82 that serves as a first output terminal of the small board 90 and is connected to the needle 78. The ground line is connected to the mesh shield 98 of the coaxial cable 82, which serves as a second output terminal of the small board 90.

The circuit including the coil 104 and the capacitor 106 on the small board 90 serves as an impedance matching circuit for substantially equalizing the input impedance of the coaxial connector 84 and the output impedance of the microwave generator 29 at a time when the microwave generator 29 is connected to the coaxial connector 84 and while the needle 78 pierces the living body 14. When the input impedance of the coaxial connector 84 and the output impedance of the microwave generator 29 are matched in this manner, reflections at the junction (indicated by the broken line 110) between the external coaxial cable 88 and the manipulator 10c are reduced, so that energy is supplied efficiently to the needle 78.

Figure 8:
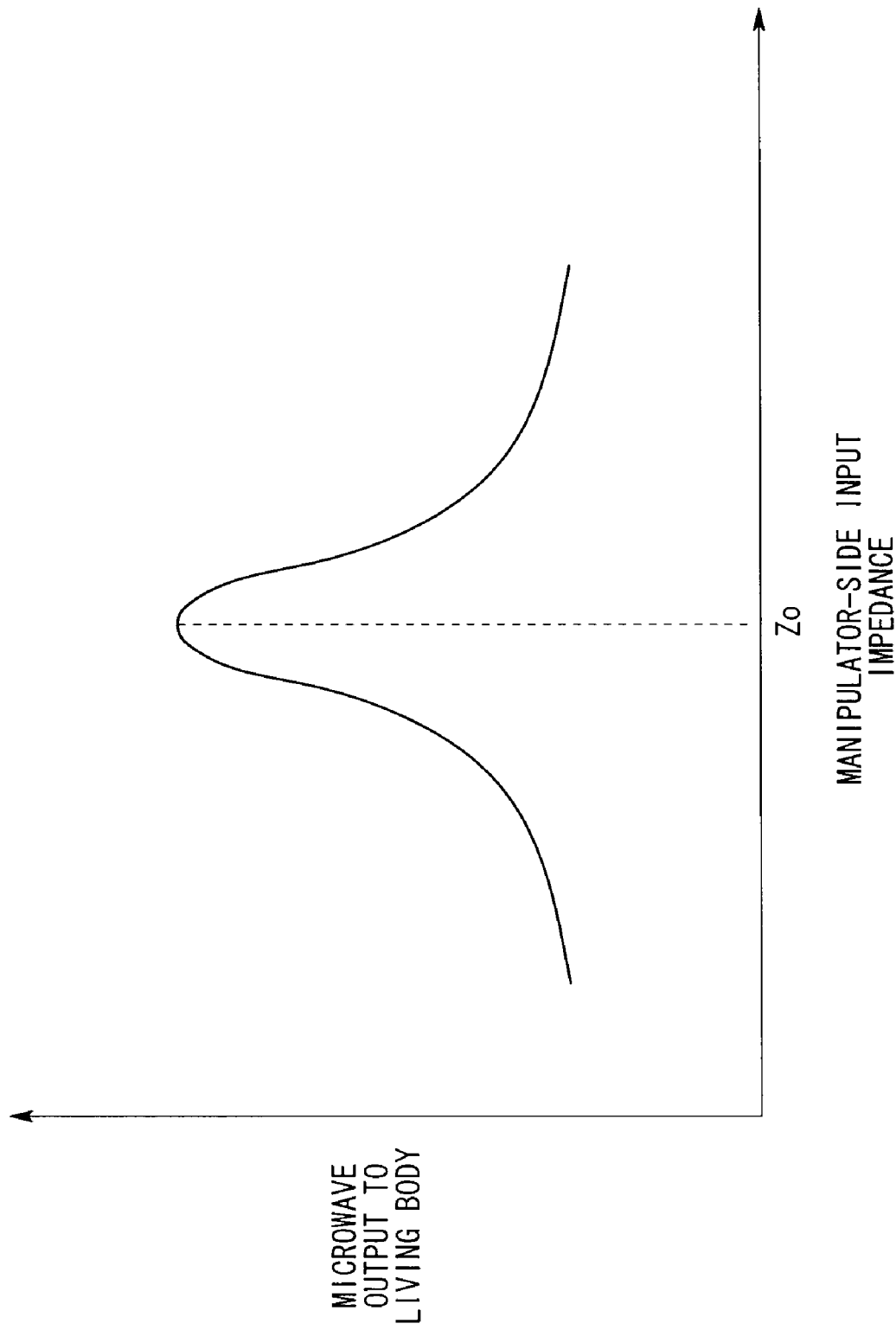
FIG. 8 is a graph showing characteristics of an impedance matching circuit.

As shown in FIG. 8, the impedance matching circuit may have characteristics thereof set such that the combined impedance of the coaxial cable 82 and the living body 14 matches the characteristic impedance $Z_0$ of the external coaxial cable 88. Since the combined impedance can be measured using an impedance analyzer, which is connected to the coaxial connector 84 while the needle 78 pierces the living body 14, the inductive and capacitive values of the coil 104 and the capacitor 106 can be selected based on the measured impedance.

As is well known in the art, when a high-frequency electric signal is applied at a junction to a terminal end having a different characteristic impedance, microwaves are reflected at the junction, thereby causing a transmission loss. However, since impedance matching is achieved by the coil 104 and the capacitor 106 on the small board 90, the manipulator 10c can reduce any transmission loss and can effectively supply microwaves. Inasmuch as the characteristic impedance of the coaxial cable 82 can freely be set without any need for matching the impedance of the external coaxial cable 88, the coaxial cable 82 may be of a small diameter. Since the coaxial cable 82 may be set to a substantially small diameter, the coaxial cable 82 need not be inserted in the joint shaft 44, but may be disposed along an outer surface of the joint shaft 44. Therefore, the coaxial cable 82 is reliably prevented from coming into contact with the wires 50a, 50b.

The small board 90 may have the circuit constants thereof adjustable by using a trimmer-type coil 104, or alternatively, may be of a replaceable structure such as a cartridge for replacement with another board having different circuit constants, so that the impedance can be adjusted depending on the state in which the manipulator is used, e.g., the frequency being used, the patient, and the affected region of the patient. If the small board 90 is removable, then the manipulator 10c can easily be cleaned, and moreover the level of resistance of the small board 90 against water and rust can be made lower.

A process of applying microwaves from the manipulator 10c to the affected region during an endoscopic surgical operation shall be described below.

The joint shaft 44 of the manipulator 10c is inserted through the trocar 25 into the body cavity 27. At this time, the yaw axis 74 and the pitch axis 76 are set to initial states, so as to orient the needle 78 coaxially with the joint shaft 44 for easily introducing the needle 78 through the trocar 25 into the body cavity 27.

The coaxial cable 82 and the joint shaft 44 through which the coaxial cable 82 extends are sufficiently small in diameter, and hence can easily be inserted through the trocar 25.

Figure 9:
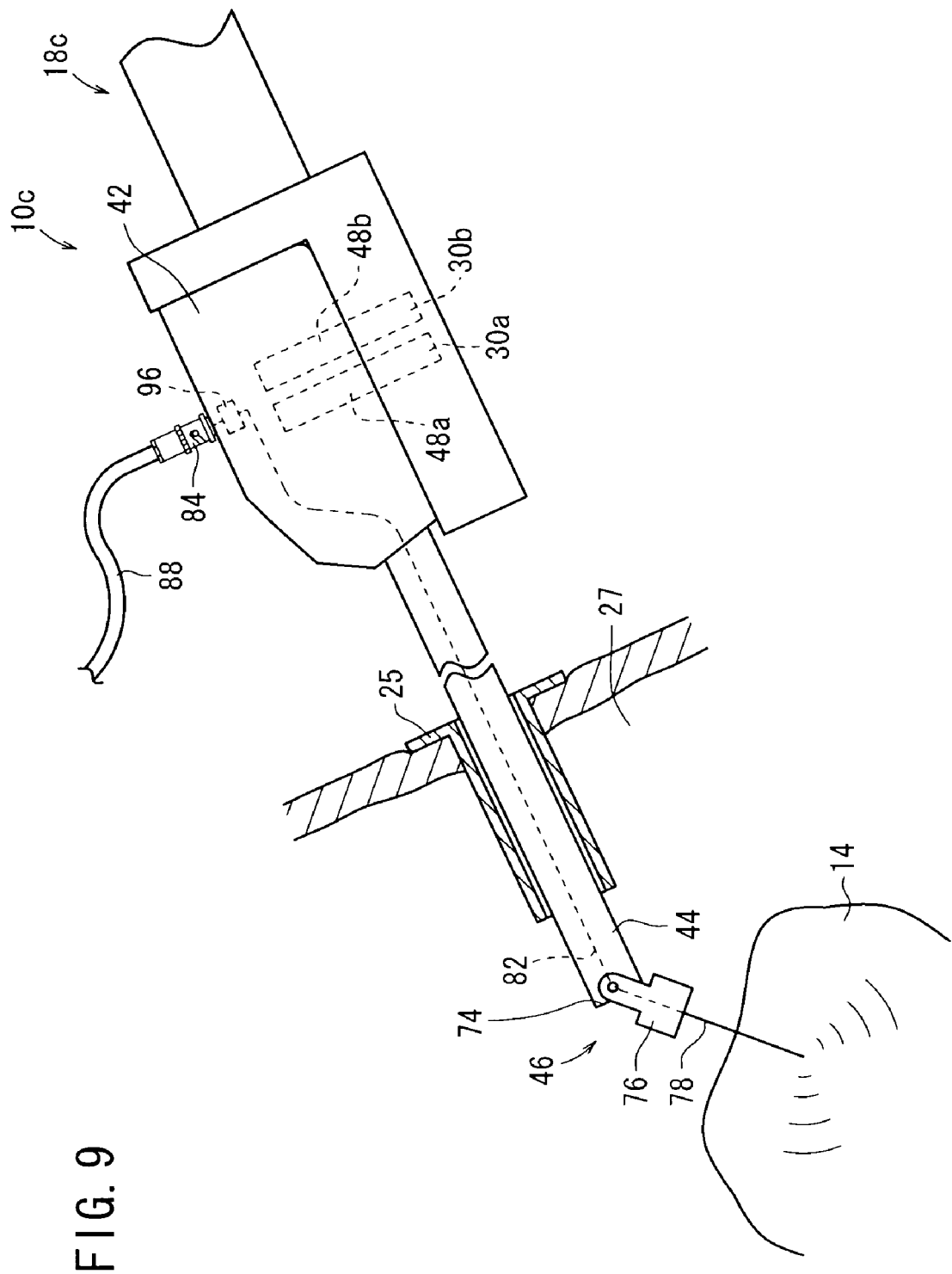
FIG. 9 is a view showing the manner in which the medical manipulator pierces a living body with a needle and supplies the needle with microwaves.

As shown in FIG. 9, the distal-end working unit 46 is angularly adjusted in order to orient the needle 78 appropriately, e.g., at a right angle, with respect to the affected region or a nearby region in the living body 14. Since the yaw axis 74 and the pitch axis 76 of the distal-end working unit 46 are disposed quite closely to the needle 78, it is easy to adjust the orientation of the needle 78, even after the needle 78 is brought in close proximity to the affected region. Thereafter, the manipulator 10c is operated to pierce the affected region or a nearby region with the needle 78. The surgeon performs the above surgical technique while watching the displayed image from the endoscope 24.

Then, the surgeon operates a switch (not shown) to supply microwaves from the microwave generator 29 to the needle 78, which applies such microwaves to the living body 14. The microwaves applied to the living body 14 are absorbed by water contained within the living body 14, and heat the water in order to thermally modify the living tissue. Living tissue irradiated with microwaves is not carbonized, but is solidified or bleeding is stopped therein. Microwaves can efficiently treat the local affected region of the living tissue, from a surface layer to a deep layer thereof, without scattering cancer tissues around.

Although the joint shaft 44 has a certain length, since the core wire 92 for transmitting microwaves to the needle 78 is shielded by the mesh shield 98, microwave energy is prevented from being unduly radiated from the core wire 92, and hence microwave energy can efficiently be supplied to the needle 78.

Since impedance matching is achieved by the circuit of the coil 104 and the capacitor 106, which are provided on the small board 90, any microwave reflections are small, thereby allowing microwave energy to be efficiently supplied to the needle 78. The impedance matching circuit is highly efficient due to the fact that its impedance matching covers the impedance of the living body 14.

When a living tissue is progressively cauterized, the living tissue is altered and the impedance thereof is varied. Therefore, the combined impedance of the coaxial cable 82 and the living body 14 shifts from an initial value $Z_0$ shown in FIG. 8, thereby resulting in an impedance matching failure, which automatically reduces the microwave output level applied to the living body 14. Since the microwave output level applied to the living body 14 is reduced depending on the extent to which the living tissue is cauterized, in the present invention, the microwave output level is automatically adjusted to prevent the living tissue from being excessively cauterized.

Subsequently, the surgeon uses his or her own judgement to stop supplying microwave energy. The surgeon then removes the needle 78 from the living body 14, returns the needle 78 to its original orientation, and pulls the joint shaft 44 out from the trocar 25.

Figure 10:
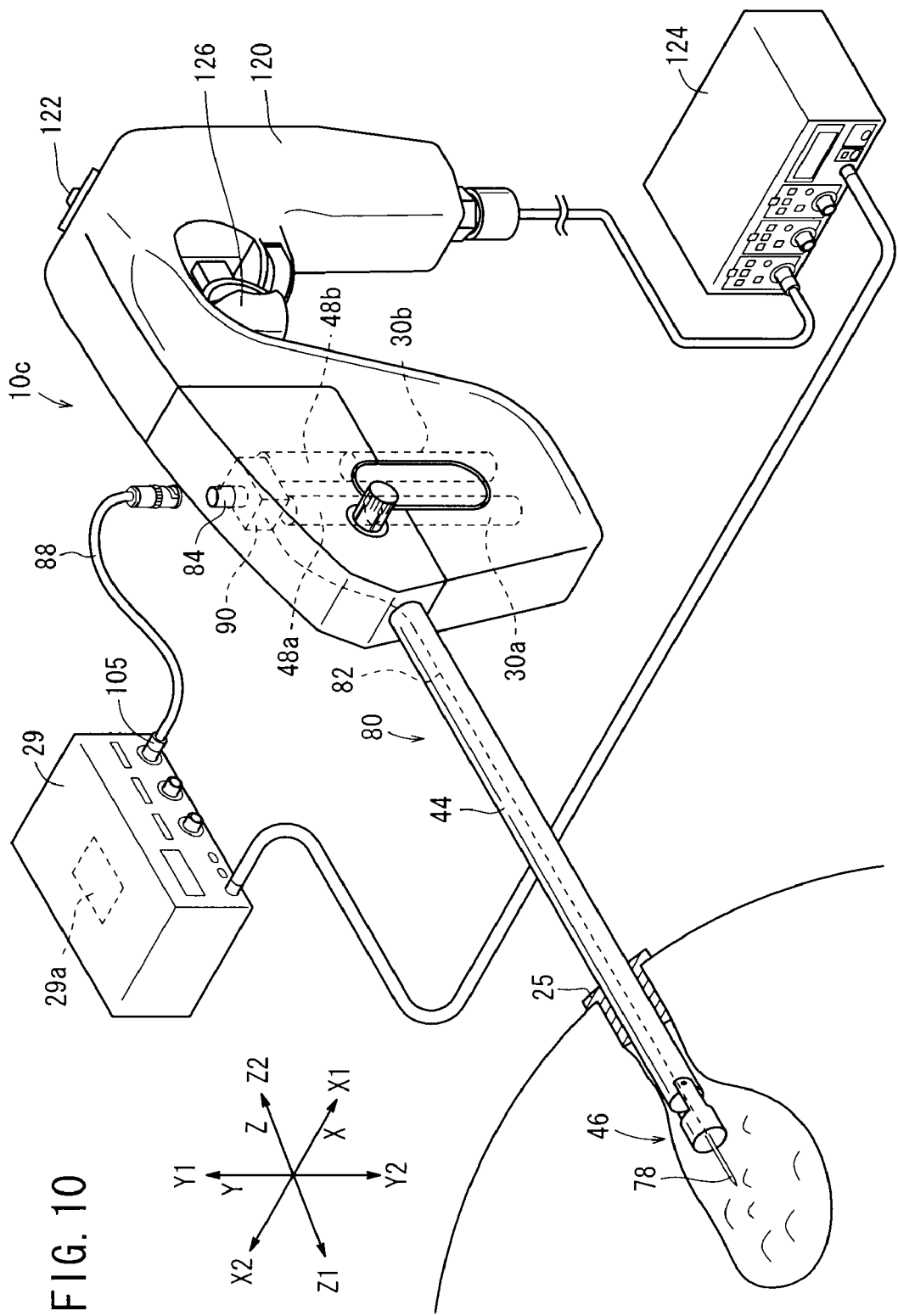
FIG. 10 is a perspective view of a directly operable medical manipulator.

Although the manipulator 10c is illustrated as being mounted on the robot arm 18c in the above embodiment, the manipulator 10c may be directly operable by the surgeon, as shown in FIG. 10. In FIG. 10, the surgeon grips a handle grip 120, and operates an input unit 122 above the handle grip 120 with a thumb or the like so as to move the distal-end working unit 46 to adjust the orientation of the needle 78. An input action made on the input unit 122 by the surgeon is read by a controller 124, which energizes the motors 30a, 30b to control the distal-end working unit 46. The handle grip 120 includes a trigger lever 126, which can be pulled by an index finger of the surgeon. An input action made on the trigger lever 126 by the surgeon is read by the controller 124, which supplies a control signal to the microwave generator 29. In response to the control signal from the controller 124, the microwave generator 29 generates and supplies microwaves from the oscillator 29a to the microwave supply means 80. Details of the microwave supply means 80 have been described above with reference to FIG. 7.

A modified manipulator 200 will be described below with reference to FIGS. 11 through 16. Those parts of the modified manipulator 200 which are identical to those of the manipulator 10c are denoted using identical reference characters, and such features will not be described in detail below.

Figure 11:
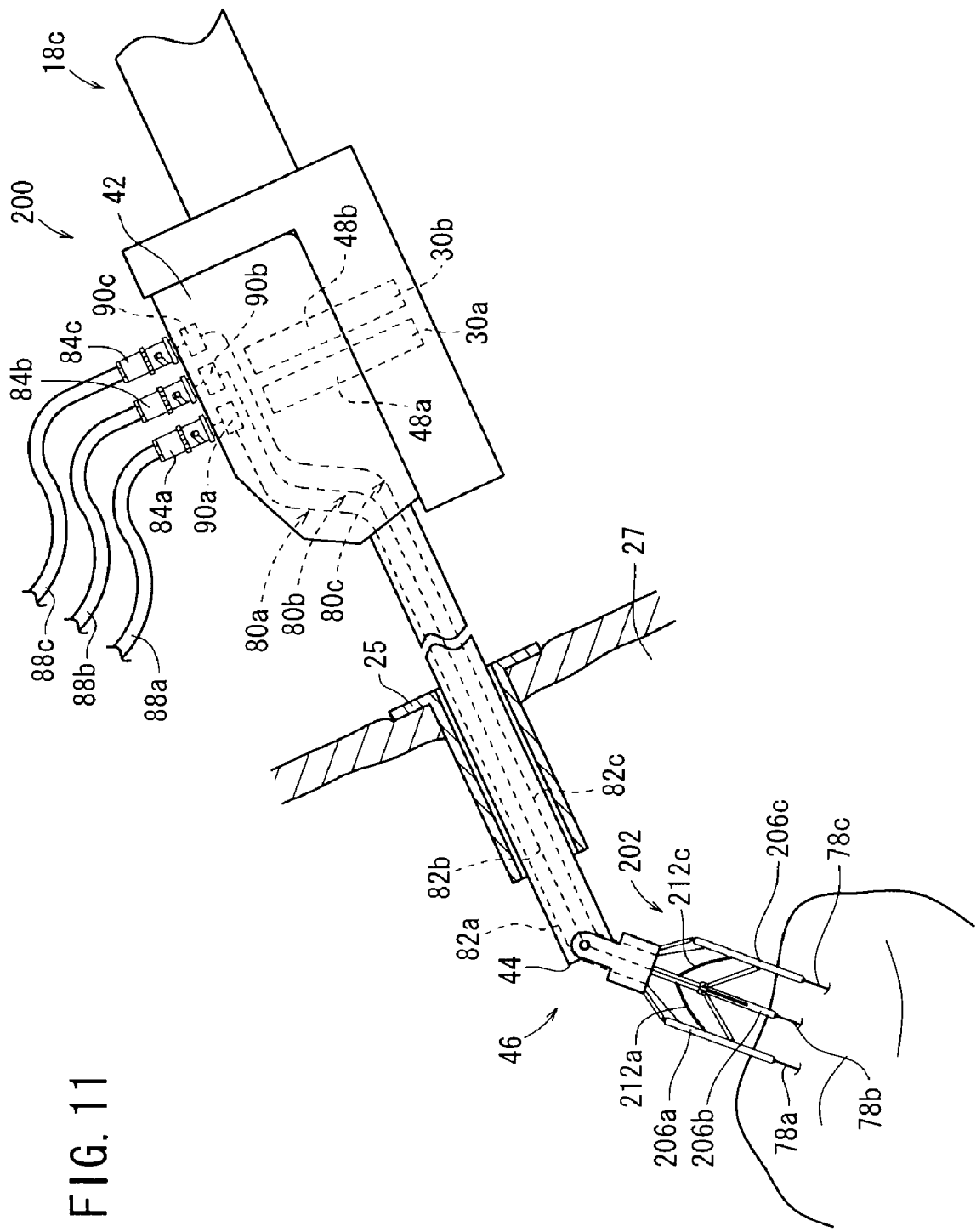
FIG. 11 is a view of a modified manipulator, showing the manner in which the manipulator pierces a living body with needles and supplies the needles with microwaves.

As shown in FIG. 11, the manipulator 200 has three independent microwave supply means 80a, 80b, 80c, each corresponding to the microwave supply means 80 referred to above. The components of the microwave supply means 80a, 80b, 80c, which correspond to the needle 78, the coaxial cable 82, the coaxial connector 84, and the small board 90 of the microwave supply means 80, are denoted by identical reference characters together with suffixes a, b, c. The microwave generator 29 is capable of supplying microwaves independently through external coaxial cables 88a, 88b, 88c to the respective microwave supply means 80a, 80b, 80c. The distal-end working unit 46 is basically of the same structure as the distal-end working unit 46 referred to above, and is adjustable in orientation. The coaxial connectors 84a, 84b, 84c are mounted in an array along the upper wall of the connecting block 42.

Figure 12:
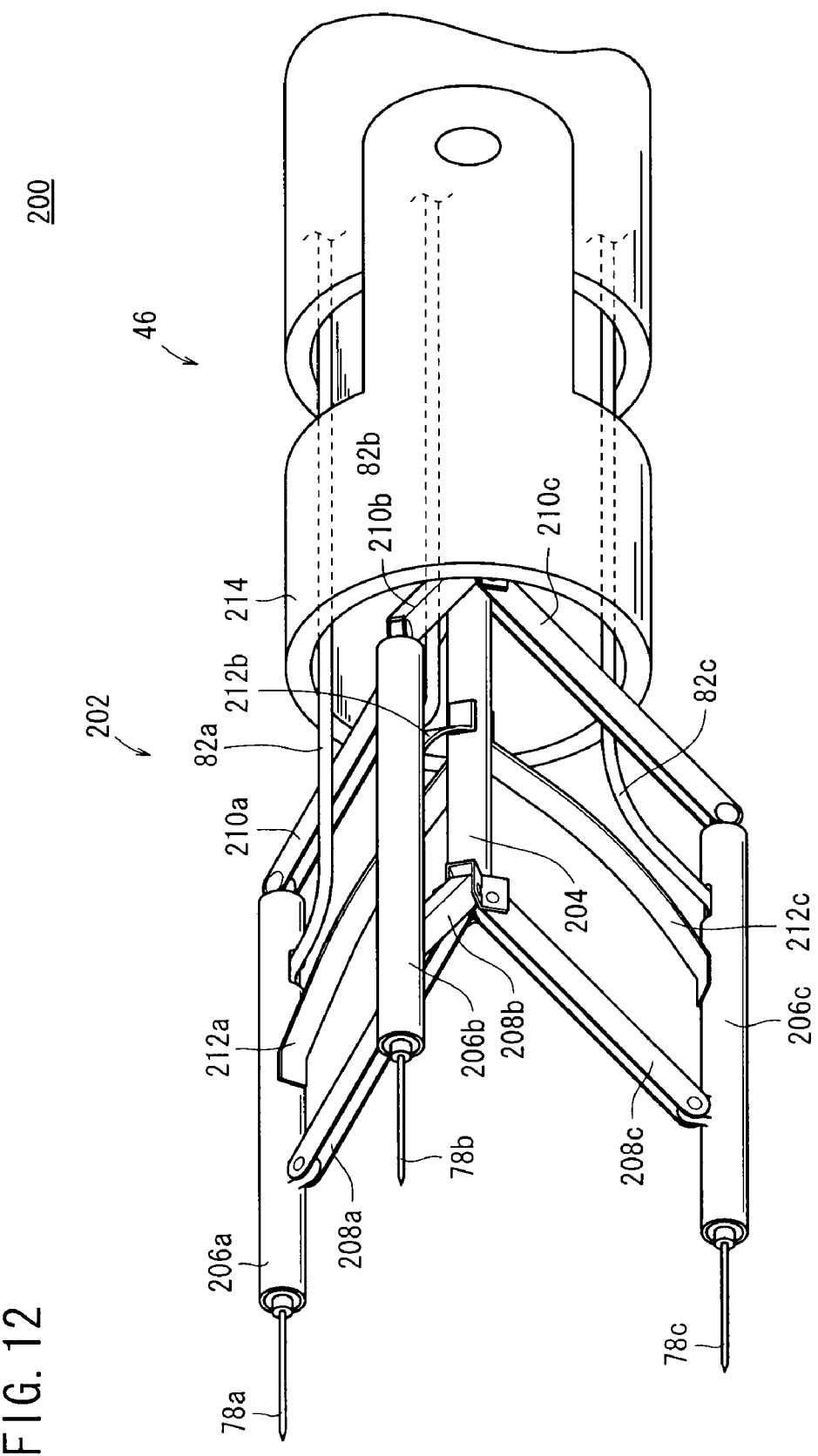
FIG. 12 is a perspective view of a needle spacing mechanism in a spread out state.

As shown in FIG. 12, the distal-end working unit 46 includes a needle spacing mechanism 202 for changing the distances between the three needles 78a, 78b and 78c.

The needle spacing mechanism 202 comprises a central support shaft 204, sleeves 206a, 206b, 206c for holding the respective needles 78a, 78b, 78c at distal ends thereof, front arms 208a, 208b, 208c and rear arms 210a, 210b, 210c by which the sleeves 206a, 206b, 206c are movably supported for movement toward and away from the central support shaft 204, and leaf springs (resilient members) 212a, 212b, 212c for normally urging the needles 78a, 78b, 78c away from each other. The needles 78a, 78b, 78c can also be urged away from each other by using other types of resilient members apart from leaf springs 212a, 212b, 212c. Coaxial cables 82a, 82b, 82c extend respectively through the sleeves 206a, 206b, 206c, and have respective core wires (not shown) connected to the needles 78a, 78b, 78c, respectively.

The front arms 208a, 208b, 208c have outer ends thereof, which are pivotally supported on intermediate portions of the sleeves 206a, 206b, 206c, respectively, and inner ends, which are pivotally supported on the distal end of the central support shaft 204. The rear arms 210a, 210b, 210c have outer ends thereof, which are pivotally supported on rear ends of the sleeves 206a, 206b, 206c, respectively, and inner ends, which are pivotally supported on the proximal end of the central support shaft 204. The front arms 208a, 208b, 208c and the rear arms 210a, 210b, 210c are equal in length to each other. The needle spacing mechanism 202 thus comprises three parallel links (link mechanisms) disposed at equal angular intervals of 120°, and the needle spacing mechanism 202 can displace the needles 78a, 78b, 78c axially while holding the needles in substantially the same orientation. The three parallel links may be ganged together for synchronous operation. The leaf springs 212a through 212c have inner ends thereof fixed to the central support shaft 204 and outer ends held slidably against inner side surfaces of the sleeves 206a, 206b, 206c, respectively, for thereby normally urging the sleeves 206a, 206b, 206c outwardly apart from each other.

The distal-end working unit 46 includes a tubular body 214 serving as a base disposed behind the needle spacing mechanism 202. The rear arms 210a, 210b, 210c can be tilted in an opening direction, until they abut against a front end face of the tubular body 214. Therefore, the tubular body 214 serves as a stopper for the parallel links. The maximum angle of the rear arms 210a, 210b, 210c with respect to the central support shaft 204 at the time the rear arms 210a, 210b, 210c abut against the front end face of the tubular body 214 may lie within a range of from 45° to 90°. When the rear arms 210a, 210b, 210c are spread away from the central support shaft 204 through such a maximum angle, the sleeves 206a, 206b, 206c and the needles 78a, 78b, 78c are positioned radially outward from the inside diameter of the trocar 25, and therefore cannot pass through the trocar 25.

Figure 13:
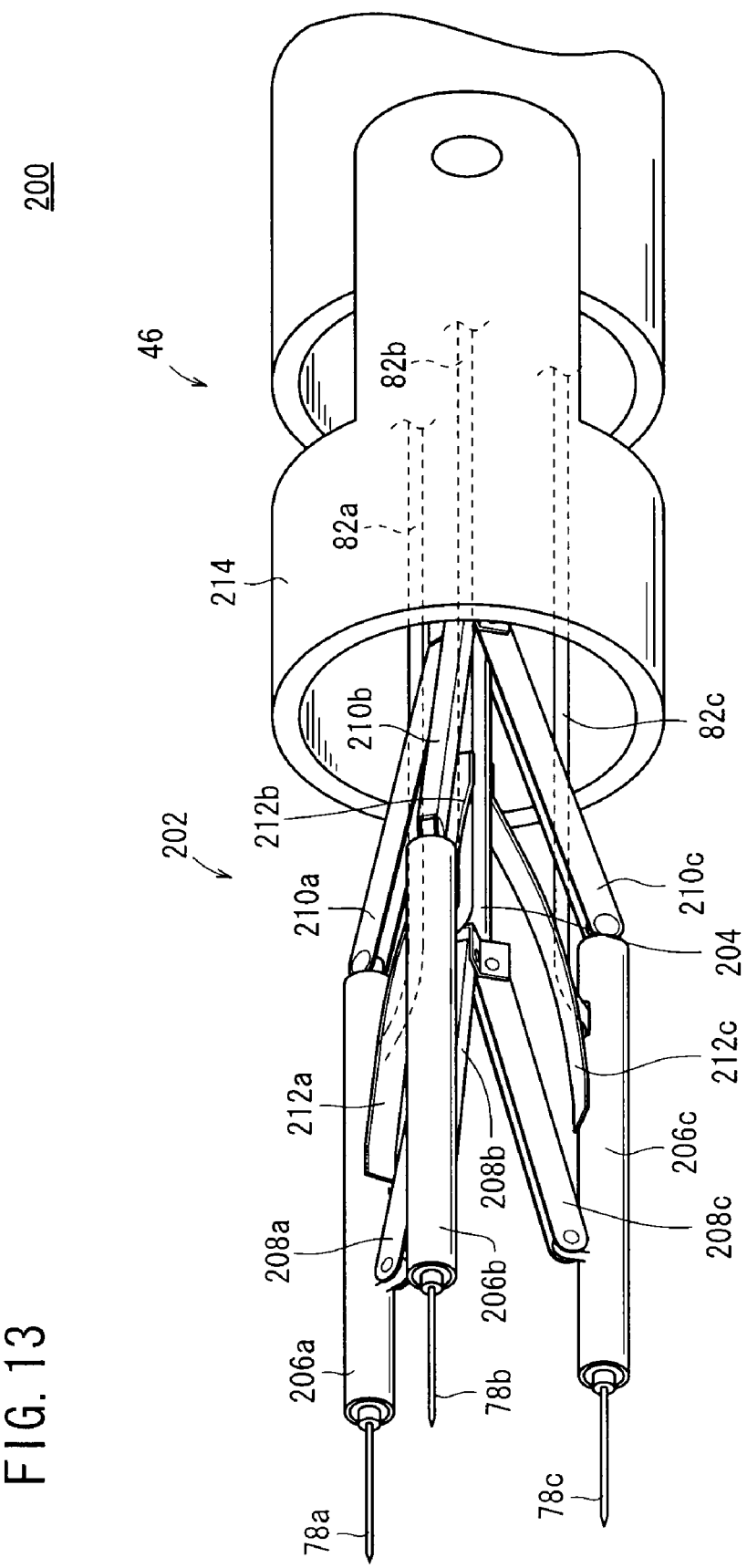
FIG. 13 is a perspective view of the needle spacing mechanism in a closed state.

As shown in FIG. 13, the needle spacing mechanism 202 can be operated to close the leaf springs 212a, 212b, 212c against the resiliency thereof, for thereby bringing the sleeves 206a, 206b, 206c and the needles 78a, 78b, 78c closely toward the central support shaft 204 until the sleeves 206a, 206b, 206c and the needles 78a, 78b, 78c are positioned radially inward from the inside diameter of the trocar 25 or from the outside diameter of the joint shaft 44. The sleeves 206a, 206b, 206c and the needles 78a, 78b, 78c can now pass through the trocar 25. The needle spacing mechanism 202 can thus be operated by the fingers of a surgeon, or by a given jig.

The needle spacing mechanism 202 is of a simple structure, which is free of actuators and a power transmitting mechanism. The needle spacing mechanism 202 is not limited to the illustrated structure for moving all the needles 78a, 78b, 78c. Rather, the needle spacing mechanism 202 may additionally include a fourth needle, which is mounted immovably on the central support shaft 204.

A process for applying microwaves from the manipulator 200 to the affected region in an endoscopic surgical operation shall be described below.

Figure 14:
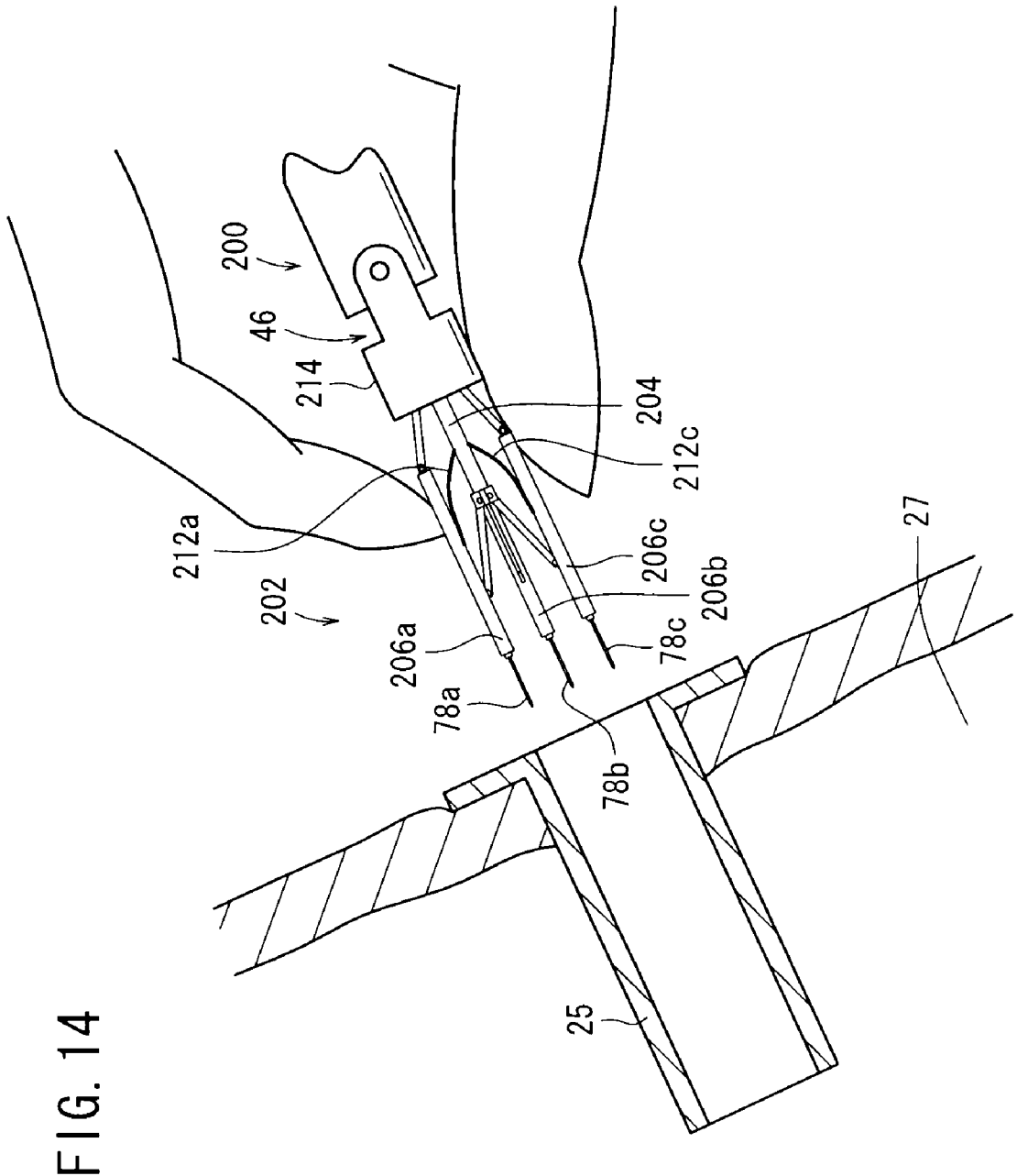
FIG. 14 is a view of the modified manipulator, showing the manner in which the needle spacing mechanism and a connector shaft are about to be inserted into a trocar.

As shown in FIG. 14, the surgeon applies his or her fingers so as to press the sleeves 206a, 206b, 206c radially inward and thereby cause the leaf springs 212a, 212b, 212c to flex against the resiliency thereof until the sleeves 206a, 206b, 206c and the needles 78a, 78b, 78c are positioned radially inward from the inside diameter of the trocar 25. Then, the surgeon inserts the needle spacing mechanism 202 and the distal-end working unit 46 into the trocar 25. The distal-end working unit 46 is held in an initial state, i.e., coaxially with the joint shaft 44.

Figure 15:
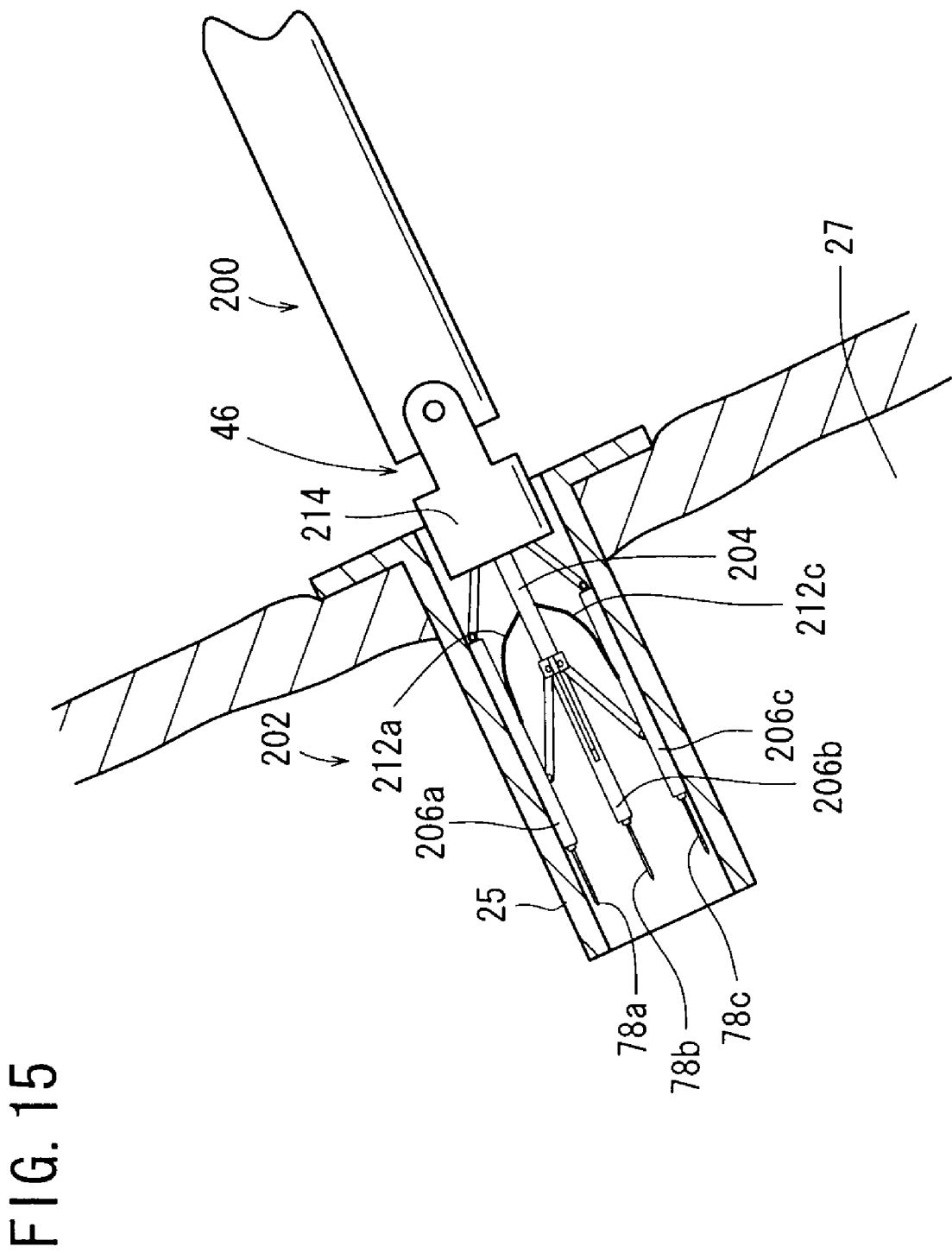
FIG. 15 is a view of the modified manipulator, showing the manner in which the needle spacing mechanism and the connector shaft are inserted into the trocar.

As shown in FIG. 15, the needle spacing mechanism 202 is spread inside the trocar 25 under the resiliency of the leaf springs 212a, 212b, 212c, thereby bringing the sleeves 206a, 206b, 206c into sliding contact with the inner wall surface of the trocar 25. Thus, the needle spacing mechanism 202 and the distal-end working unit 46 can easily pass through the trocar 25.

When the needle spacing mechanism 202 is displaced out of the trocar 25 into the body cavity 27, the leaf springs 212a, 212b, 212c spring back outwardly to cause the needle spacing mechanism 202 to spread automatically until the rear arms 210a, 210b, 210c abut against the front end face of the tubular body 214. Thus, the three needles 78a, 78b, 78c are appropriately spaced apart from each other while being maintained in parallel with each other.

As shown in FIG. 11, the surgeon adjusts the orientation of the distal-end working unit 46 in order to orient the needles 78a, 78b, 78c appropriately, e.g., substantially perpendicularly, with respect to the affected region or a nearby region within the living body 14. Then, the surgeon pushes the needles 78a, 78b, 78c to pierce the living body 14.

Then, the surgeon operates a switch (not shown) in order to supply microwaves from the microwave generator 29 to the needles 78a, 78b, 78c, which apply the microwaves to the living body 14 to cauterize the same. Since the needles 78a, 78b, 78c are spaced apart from each other, the needles can pierce spaced locations and can efficiently perform a surgical technique over a wide area for a synergetic effect. Since the needles 78a, 78b, 78c are held in parallel with each other, the needles can easily pierce the living body 14.

Figure 16:
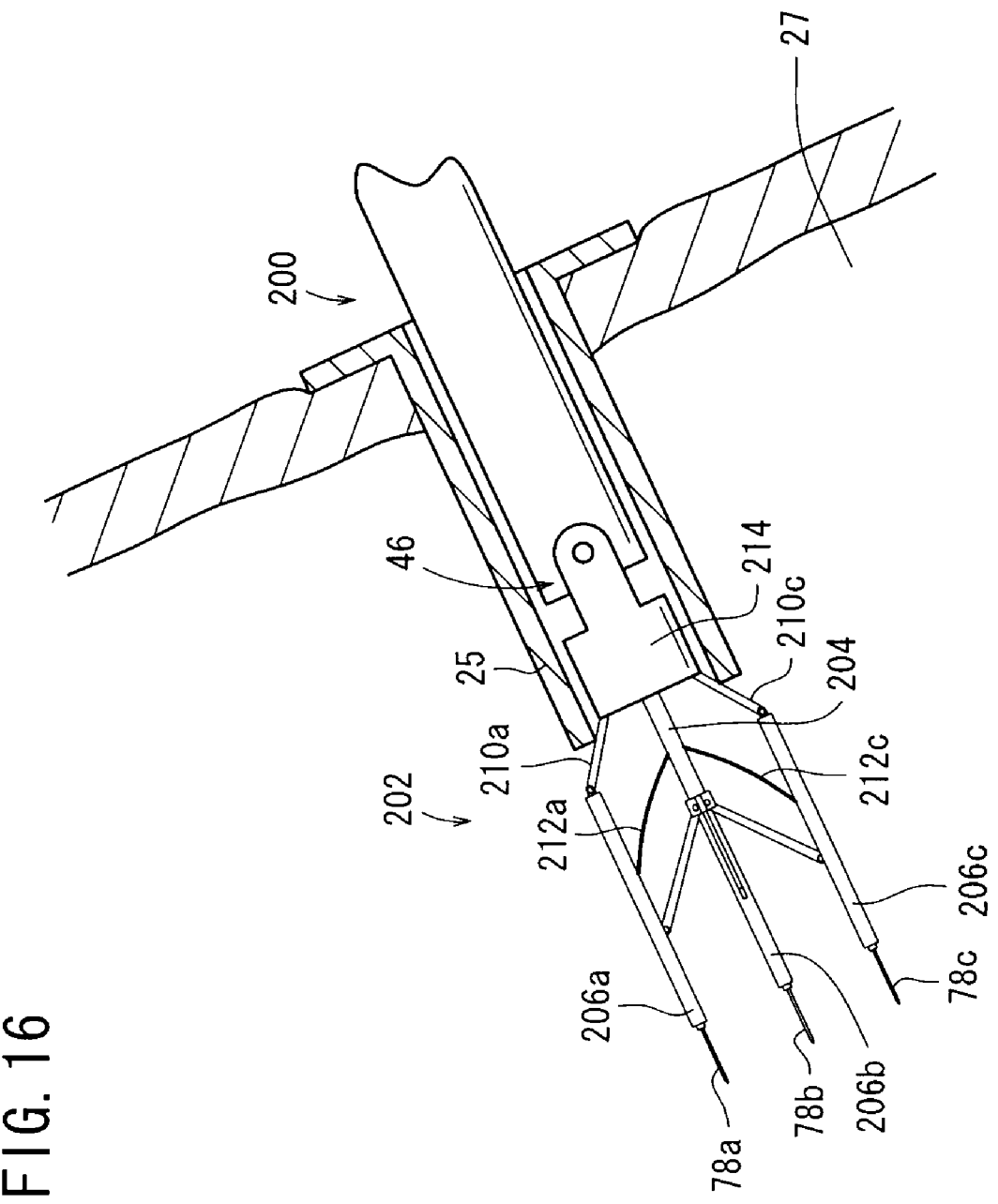
FIG. 16 is a view of the modified manipulator, showing the manner in which the needle spacing mechanism and the connector shaft are about to be pulled out from the trocar.

After the pierced living body 14 has been cauterized, the surgeon stops the supply of microwaves, removes the needles 78a, 78b, 78c from the living body 14, returns the distal-end working unit 46 to its original orientation, and pulls the joint shaft 44 out from the trocar 25. At this time, as shown in FIG. 16, the rear arms 210a, 210b, 210c of the needle spacing mechanism 202 abut against the end face of the trocar 25 and are tilted radially inward, so that the needles 78a, 78b, 78c are moved radially back toward the central support shaft 204 until the sleeves 206a, 206b, 206c and the needles 78a, 78b, 78c are positioned radially inward from the inside diameter of the trocar 25. The joint shaft 44 and the needles 78a, 78b, 78c can now easily be pulled out from the trocar 25.

Figure 17A:
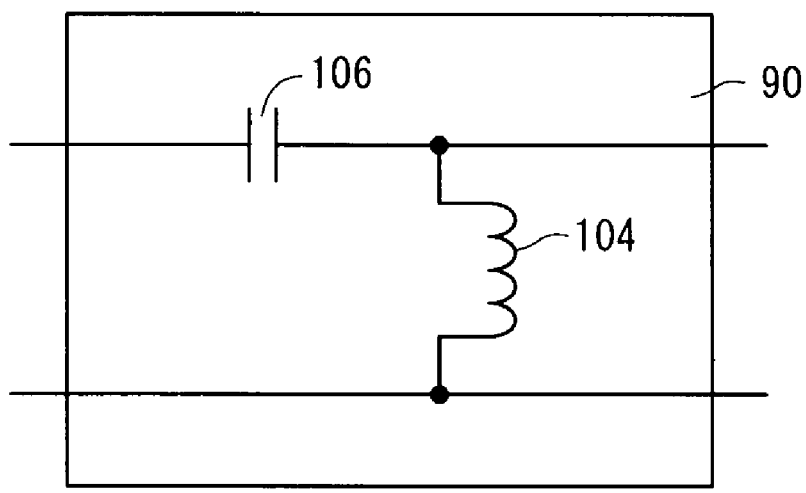
FIG. 17A is a circuit diagram of a small board according to a first modification.
Figure 17B:
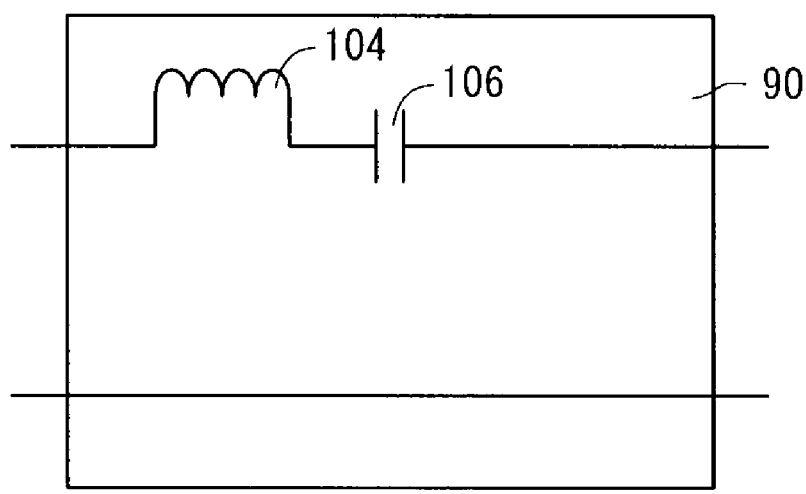
FIG. 17B is a circuit diagram of a small board according to a second modification.

The impedance matching circuit on the small board 90 is not limited to the circuit arrangement shown in FIG. 7, but may be arranged in other ways, insofar as the impedance matching circuit matches the characteristic impedance $Z_0$ of the external coaxial cable 88. For example, as shown in FIG. 17A, the capacitor 106 and the coil 104 may be switched around, or as shown in FIG. 17B, the capacitor 106 and the coil 104 may be connected in series with each other.

Figure 18:
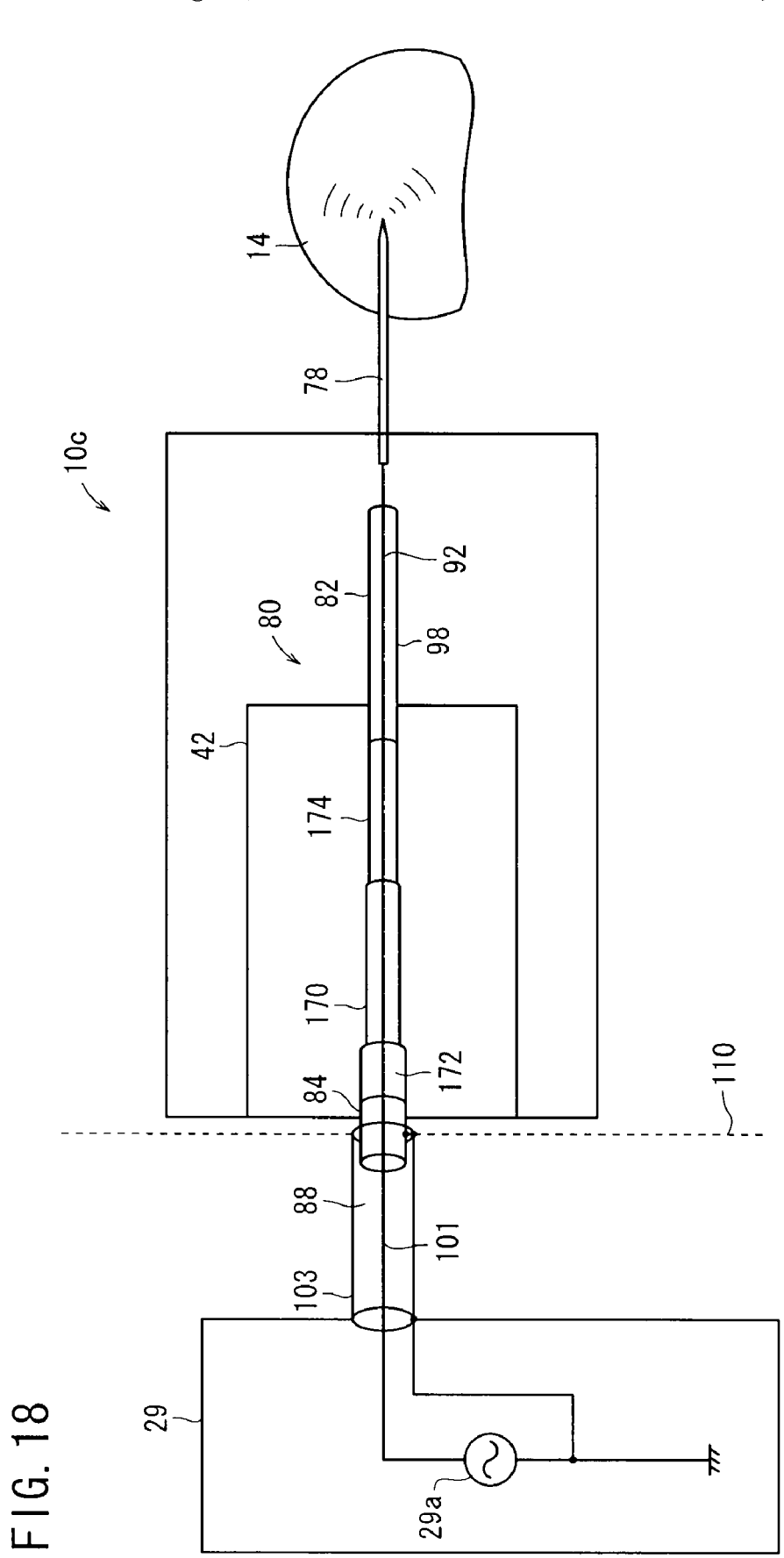
FIG. 18 is a circuit diagram of a microwave supply means of a medical manipulator, in which metal pipes are used as an impedance matching circuit.

Impedance matching may be achieved by any suitable capacitive means and inductive means, apart from the capacitor 106 and the coil 104. For example, as shown in FIG. 18, a metal pipe 170 coaxial with the core wire 92 may be used at least as a portion of the impedance matching circuit within the connecting block 42.

Figure 19:
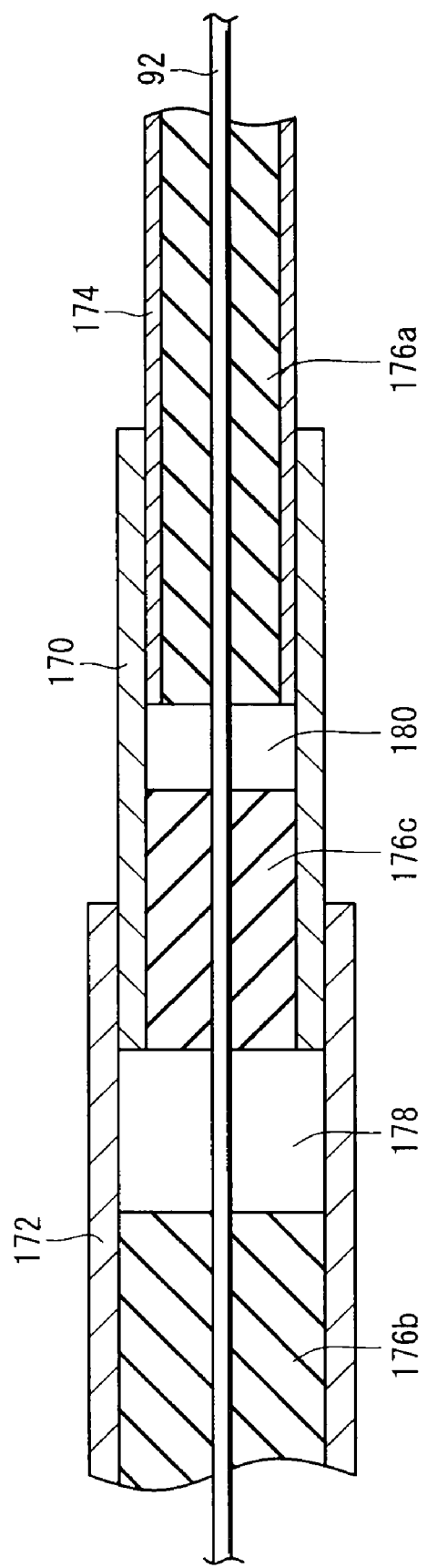
FIG. 19 is a cross-sectional view of the metal pipes, which serve as the impedance matching circuit, and associated parts thereof.

More specifically, as shown in FIG. 19, the metal pipe 170 is interposed between a fixed metal shield pipe 172 and a metal shield pipe 174. The metal shield pipe 172 is connected to the coaxial connector 84, whereas the metal shield pipe 174 is connected to the mesh shield 98. The metal pipe 170 has an outer surface held in sliding engagement with an inner surface of the metal shield pipe 172, and an inner surface held in sliding engagement with an outer surface of the metal shield pipe 174. The interior of the metal shield pipe 174 is filled with an insulating body 176a. The metal shield pipe 172 is filled with an insulating body 176b, while leaving a space 178 in which the metal shield pipe 170 is movable to the left as shown in FIG. 19. The metal pipe 170 is filled with an insulating body 176c, while leaving a space 180 in which the metal shield pipe 174 is movable to the left as shown in FIG. 19. An appropriate clearance is provided between the insulating bodies 176a, 176b, 176c and the core wire 92, thereby allowing the metal pipe 170 to move in unison with the insulating body 176c. When the metal pipe 170 slides with respect to the metal shield pipes 172, 174, the spaces 178, 180 vary so as to vary capacitive components thereof, for achieving a desired impedance matching in combination with inductive components, not shown. Alternatively, the impedance matching circuit may be constructed on the basis of the description given in the literature referred to above, "Improvement on the input impedance of a coaxial-slot antenna for interstitial heating by loading a matching circuit", by Shinya Okabe and three others, IECEI transactions 2004/10, Vol. J87-B, No. 10, pp. 1741-1748.

Although certain preferred embodiments of the present invention have been shown and described in detail, it should be understood that various changes and modifications may be made to the embodiments without departing from the scope of the invention as set forth in the appended claims.

What is claimed is:

1. A medical manipulator comprising:
   a shaft;
   a plurality of needles mounted on a distal end of said shaft; and
   needle spacing means for spacing said needles apart from each other, the needle spacing means including
      a support shaft,
      a plurality of sleeves disposed along a circumferential direction of the support shaft, the plurality of sleeves respectively holding the plurality of needles, and
      resilient members disposed between respective sleeves and the support shaft, the resilient members urging the respective sleeves outwardly in a radial direction from the support shaft.

2. The medical manipulator according to claim 1, wherein said needle spacing means further includes link mechanisms for displacing said needles while substantially maintaining an orientation of said needles with respect to each other.

3. The medical manipulator according to claim 1, wherein said needle spacing means further includes arms, which are tiltable so as to return said needles closely toward each other in abutment against an end of a trocar when said shaft is pulled out of said trocar.

4. A medical robot system comprising:
   a medical manipulator including
      a shaft,
      at least one joint mounted on a distal end of said shaft, the joint being actuatable by an actuator,
      a plurality of needles mounted on the distal end of said shaft, and
      needle spacing means for spacing said needles apart from each other, the needle spacing means including
         a support shaft,
         a plurality of sleeves disposed along a circumferential direction of the support shaft, the plurality of sleeves respectively holding the plurality of needles, and
         resilient members disposed between respective sleeves and the support shaft, the resilient members urging the respective sleeves outwardly in a radial direction from the support shaft;
   a robot arm holding said medical manipulator; and
   a controller for controlling said medical manipulator and said robot arm.

5. The medical manipulator according to claim 1, wherein the plurality of sleeves are disposed at equal angular intervals along the circumferential direction of the support shaft.

6. The medical manipulator according to claim 1, further comprising:
   at least one joint mounted on the distal end of said shaft, the joint being actuatable by an actuator;
   a connector disposed at a proximal end of the manipulator; and a conductor including a coaxial cable providing at least a portion of an electrical connection between said connector and the plurality of needles, for supplying microwaves to the plurality of needles.

7. The medical manipulator according to claim 6, wherein said coaxial cable is disposed at least in said shaft or on a portion along said shaft.

8. The medical manipulator according to claim 6, wherein said coaxial cable includes first and second poles, the first pole including an external tubular covering conductor, at least a portion of which includes a metal tube.

9. The medical manipulator according to claim 6, further comprising a circuit interposed between said connector and said coaxial cable, said circuit including a metal pipe.

10. The medical manipulator according to claim 6, wherein said plurality of needles cauterizes a living tissue of a living body when said needles are supplied with microwaves while piercing said living body.

11. The medical manipulator according to claim 6, further comprising a connecting block having a housing from which the shaft extends,
    wherein the connector is fixed to a wall of the housing and includes a coupling portion that is coupled to an external coaxial cable.

12. The medical manipulator according to claim 6, further comprising a circuit interposed between said connector and said coaxial cable, said circuit including inductive means and capacitive means.

13. The medical manipulator according to claim 12, further comprising a microwave oscillation source connected to said connector,
    wherein said circuit further includes a matching circuit for substantially equalizing an output impedance of said microwave oscillation source and an input impedance of said coaxial connector, while said needle pierces a living body.

* * * * *